(12) United States Patent
Suzuki et al.

(10) Patent No.: US 8,929,627 B2
(45) Date of Patent: Jan. 6, 2015

(54) EXAMINATION INFORMATION DISPLAY DEVICE AND METHOD

(75) Inventors: Masato Suzuki, Tokyo (JP); Maiko Kawase, Tokyo (JP); Yayoi Shitara, Tokyo (JP); Yuki Fukuyama, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 193 days.

(21) Appl. No.: 13/638,591

(22) PCT Filed: Mar. 23, 2011

(86) PCT No.: PCT/JP2011/056880
§ 371 (c)(1),
(2), (4) Date: Dec. 17, 2012

(87) PCT Pub. No.: WO2011/122402
PCT Pub. Date: Oct. 6, 2011

(65) Prior Publication Data
US 2013/0088512 A1    Apr. 11, 2013

(30) Foreign Application Priority Data

Mar. 31, 2010   (JP) .................. 2010-081772

(51) Int. Cl.
| | |
|---|---|
| G06K 9/00 | (2006.01) |
| G09G 5/377 | (2006.01) |
| A61B 6/00 | (2006.01) |
| G06F 19/00 | (2011.01) |
| G06Q 10/06 | (2012.01) |
| G06Q 50/22 | (2012.01) |
| A61B 5/055 | (2006.01) |
| A61B 6/03 | (2006.01) |

(52) U.S. Cl.
CPC .............. *G09G 5/377* (2013.01); *A61B 6/463* (2013.01); *G06F 19/322* (2013.01); *G06Q 10/06* (2013.01); *G06Q 50/22* (2013.01); *A61B 5/055* (2013.01); *A61B 6/03* (2013.01)
USPC .......................................... 382/128; 382/629

(58) Field of Classification Search
USPC ........ 345/629; 348/333.05; 378/63; 382/128, 382/132; 386/241; 600/410; 715/838
See application file for complete search history.

(56) References Cited

U.S. PATENT DOCUMENTS

| | | | |
|---|---|---|---|
| 2009/0054755 A1* | 2/2009 | Shiibashi ....................... | 600/407 |
| 2012/0029943 A1* | 2/2012 | Kurahashi ........................ | 705/3 |

FOREIGN PATENT DOCUMENTS

| | | |
|---|---|---|
| JP | 2001-308859 | 11/2001 |
| JP | 2002-342696 | 11/2002 |

(Continued)

OTHER PUBLICATIONS

International Search Report from International Application No. PCT/JP2011/056881 mailed May 10, 2011.

*Primary Examiner* — Gregory F Cunningham
(74) *Attorney, Agent, or Firm* — Brundidge & Stanger, P.C.

(57) ABSTRACT

An examination information display device of the present invention includes: a storage unit that stores examination information of an object; a display unit that has a display screen on which the examination information is displayed; an extraction unit that extracts candidate examination information, which is a candidate referred to or compared with a reference examination to be diagnosed, using supplementary information of the examination information of the object stored in the storage unit; and a display control unit that displays the candidate examination information in a predetermined display region of the display screen.

16 Claims, 22 Drawing Sheets

(56) References Cited

FOREIGN PATENT DOCUMENTS

| JP | 2004-005565 | 1/2004 |
| JP | 2005-253641 | 9/2005 |
| JP | 2006006671 A * | 1/2006 | ............ A61B 5/00 |
| JP | 2006-268120 | 10/2006 |
| JP | 2006-271541 | 10/2006 |
| JP | 2007-233841 | 9/2007 |
| JP | 2009-230304 | 10/2009 |

* cited by examiner

FIG. 4

USER NAME          HITACHI Dr
ROUTINE NAME       COLON CANCER
EXAMINATION TYPE   CT IMAGE
SCANNED PORTION    ABDOMEN

| READING PROTOCOL | SCANNED PORTION | SCANNED PORTION AND EXAMINED PORTION | COMMENT |
|---|---|---|---|
| REFERENCE CANDIDATE 1 | CR IMAGE | CHEST | NO ABNORMALITIES IN CHEST RADIOGRAPHS? |
| REFERENCE CANDIDATE 2 | CT IMAGE | ABDOMEN | CURATIVE EFFECT HAS BEEN VERIFIED BY PAST COMPARISON |
| REFERENCE CANDIDATE 3 | TV | HEART | EMBOLIZED PORTION CHECK |
| REFERENCE CANDIDATE 4 | MRI IMAGE | HEAD | METASTASIS CHECK |
| REFERENCE CANDIDATE 5 | BLOOD TEST | NEWEST RESULT | HAS TUMOR MARK IMPROVED? |
| REFERENCE CANDIDATE 6 | BLOOD TEST | SAME TYPE AS REFERENCE CANDIDATE 5 | COMPARED WITH THIS |
| REFERENCE CANDIDATE 7 | ELECTROCARDIOGRAM | ... | ... |

LAYOUT1

| REFERENCE CANDIDATE1 | REFERENCE CANDIDATE2 | REFERENCE CANDIDATE5 |
|---|---|---|
| | | REFERENCE CANDIDATE6 |
| REFERENCE CANDIDATE4 | REFERENCE CANDIDATE3 | REFERENCE CANDIDATE7 |

LAYOUT2

| REFERENCE CANDIDATE1 | REFERENCE CANDIDATE2 | REFERENCE CANDIDATE6 |
|---|---|---|
| | | REFERENCE CANDIDATE5 |
| REFERENCE CANDIDATE4 | REFERENCE CANDIDATE3 | REFERENCE CANDIDATE7 |

LAYOUT3

| REFERENCE CANDIDATE1 | REFERENCE CANDIDATE5 | REFERENCE CANDIDATE6 |
|---|---|---|
| | | REFERENCE CANDIDATE4 |
| REFERENCE CANDIDATE2 | REFERENCE CANDIDATE3 | REFERENCE CANDIDATE7 |

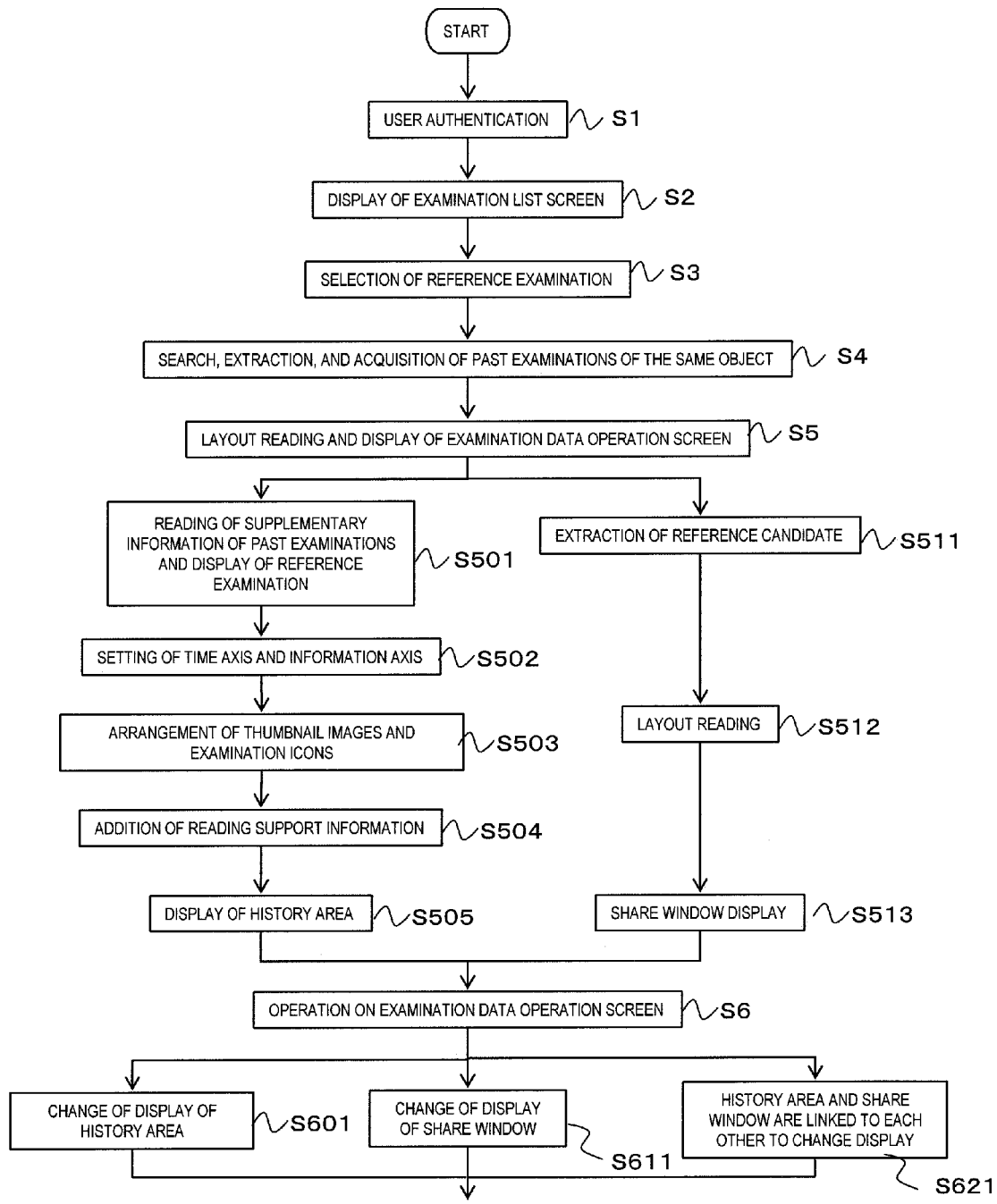

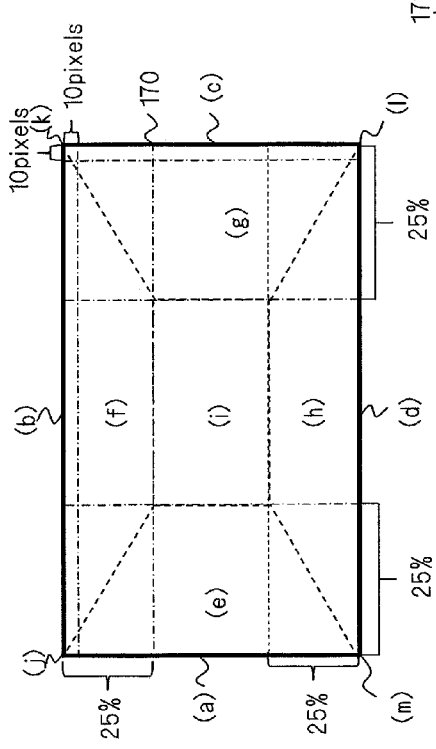

FIG. 17

| | |
|---|---|
| a (ON BORDERLINE) | ADDED TO LEFT SIDE OF IMAGE (AUTOMATIC ADJUSTMENT OF DISPLAY AREA WIDTH) |
| b (ON BORDERLINE) | ADDED TO UPPER SIDE OF IMAGE (AUTOMATIC ADJUSTMENT OF DISPLAY AREA WIDTH) |
| c (ON BORDERLINE) | ADDED TO RIGHT SIDE OF IMAGE (AUTOMATIC ADJUSTMENT OF DISPLAY AREA WIDTH) |
| d (ON BORDERLINE) | ADDED TO LOWER SIDE OF IMAGE (AUTOMATIC ADJUSTMENT OF DISPLAY AREA WIDTH) |
| e | DIVISION OF DISPLAY AREA AND ADDITION TO LEFT SIDE OF IMAGE |
| f | DIVISION OF DISPLAY AREA AND ADDITION TO UPPER SIDE OF IMAGE |
| g | DIVISION OF DISPLAY AREA AND ADDITION TO RIGHT SIDE OF IMAGE |
| h | DIVISION OF DISPLAY AREA AND ADDITION TO LOWER SIDE OF IMAGE |
| I | IMAGE REPLACEMENT |
| j ~ m | SPLITTING IS PERFORMED ACROSS ADJACENT AREAS AND IMAGES ARE ADDED |

FIG. 18

(1) IN INITIAL STATE (STATE WHERE NO IMAGE IS DISPLAYED), THUMBNAIL IMAGE At OF IMAGE A IS DROPPED TO ONE OF POSITIONS OF a TO m.

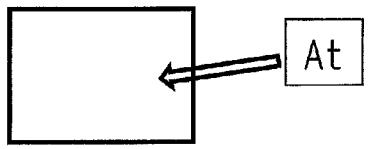

(2) IMAGE A IS DISPLAYED. HERE, THUMBNAIL IMAGE Bt OF IMAGE B IS DROPPED TO c (ON BORDERLINE).

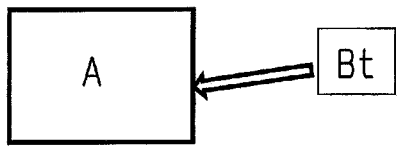

(3) IMAGE B IS ADDED TO RIGHT SIDE OF IMAGE A. IN THIS CASE, DISPLAY AREA WIDTHS OF IMAGES A AND B ARE AUTOMATICALLY ADJUSTED. HERE, (3-1) THUMBNAIL IMAGE Ct IS DROPPED TO c (ON BORDERLINE).   (3-2) THUMBNAIL IMAGE Ct IS DROPPED TO f.

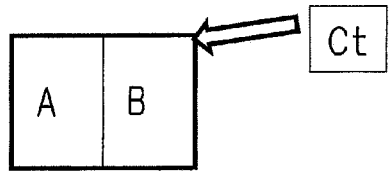    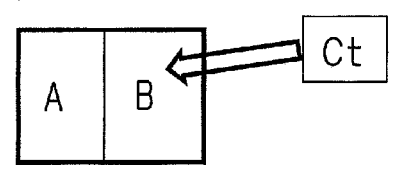

(4-1) IMAGE C IS ADDED ABOVE IMAGES A AND B.   (4-2) DIVISION OF DISPLAY AREA OF IMAGE B AND ADDITION ABOVE IMAGE B

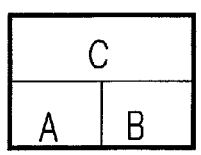    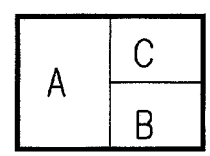

(5) THUMBNAIL IMAGE Dt OF IMAGE D IS DROPPED TO i OF IMAGE C.

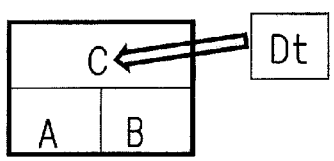    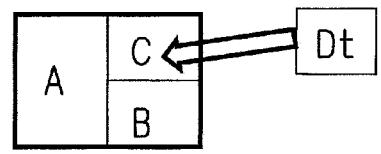

(6) IMAGE C IS REPLACED WITH IMAGE D.

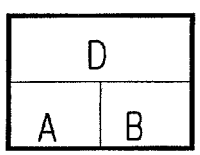    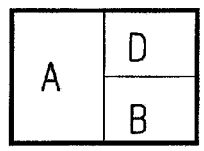

EXAMINATION INFORMATION DISPLAY DEVICE AND METHOD

TECHNICAL FIELD

The present invention relates to an examination information display device and method and, in particular, to screen display of medical images or medical examination information.

BACKGROUND ART

PTL 1 discloses a medical image reading support system which calculates a priority on the basis of the reference frequency of a medical image and displays a medical image for which a predetermined priority has been set.

CITATION LIST

Patent Literature

[PTL 1] JP-A-2006-271541

SUMMARY OF INVENTION

Technical Problem

According to PTL 1, it is possible to display a medical image according to the priority, but there has been a problem in that it is difficult to search for candidate examination information, which is a candidate referred to or compared with a reference examination to be diagnosed, in relation to the search information received for the same object.

The present invention has been made in view of the above problem, and it is an object of the present invention to provide an examination information display device and method capable of searching, specifying, and selecting the candidate examination information easily.

Solution to Problem

In order to achieve the above-described object, in the present invention, examination information which is a candidate referred to or compared with a reference examination to be diagnosed is extracted by extraction means using examination information of an object stored in storage means, and the extracted examination information is displayed in a predetermined display region of a display screen by a display control unit.

Specifically, an examination information display device related to the present invention includes a storage unit that stores examination information of an object and a display unit that has a display screen on which the examination information is displayed, and is characterized in that it includes an extraction unit that extracts candidate examination information, which is a candidate referred to or compared with a reference examination to be diagnosed, using supplementary information of the examination information of the object stored in the storage unit and a display control unit that displays the candidate examination information in a predetermined display region of the display screen.

In addition, an examination information display method related to the present invention is characterized in that it includes: a step of storing examination information of an object in a storage unit; a step of extracting candidate examination information, which is a candidate referred to or compared with a reference examination for which the stored examination information of the object is to be diagnosed, using supplementary information of the examination information of the object by means of an extraction unit; and a step of displaying the extracted candidate examination information in a predetermined display region of a display screen of a display unit by means of a display control unit.

Advantageous Effects of Invention

According to the present invention, the candidate examination information, which is a candidate referred to or compared with the reference examination for which the stored examination information of the object is to be diagnosed, is extracted using the supplementary information of the examination information of the object by means of the extraction unit, and the extracted candidate examination information is displayed in a predetermined display region of the display screen of the display unit. Therefore, it becomes easy to search, specify, and select a candidate reference examination.

BRIEF DESCRIPTION OF DRAWINGS

FIG. 4 is a schematic diagram showing an example of data stored in a reference candidate/protocol/layout storage section 33.

FIG. 5 is a flow chart showing the flow of the process of the image display system.

FIG. 17 is an explanatory view illustrating the percentages and regions of the layout division positions.

FIG. 18 is an explanatory view of the layout change based on FIG. 17.

DESCRIPTION OF EMBODIMENTS

Figure 1:
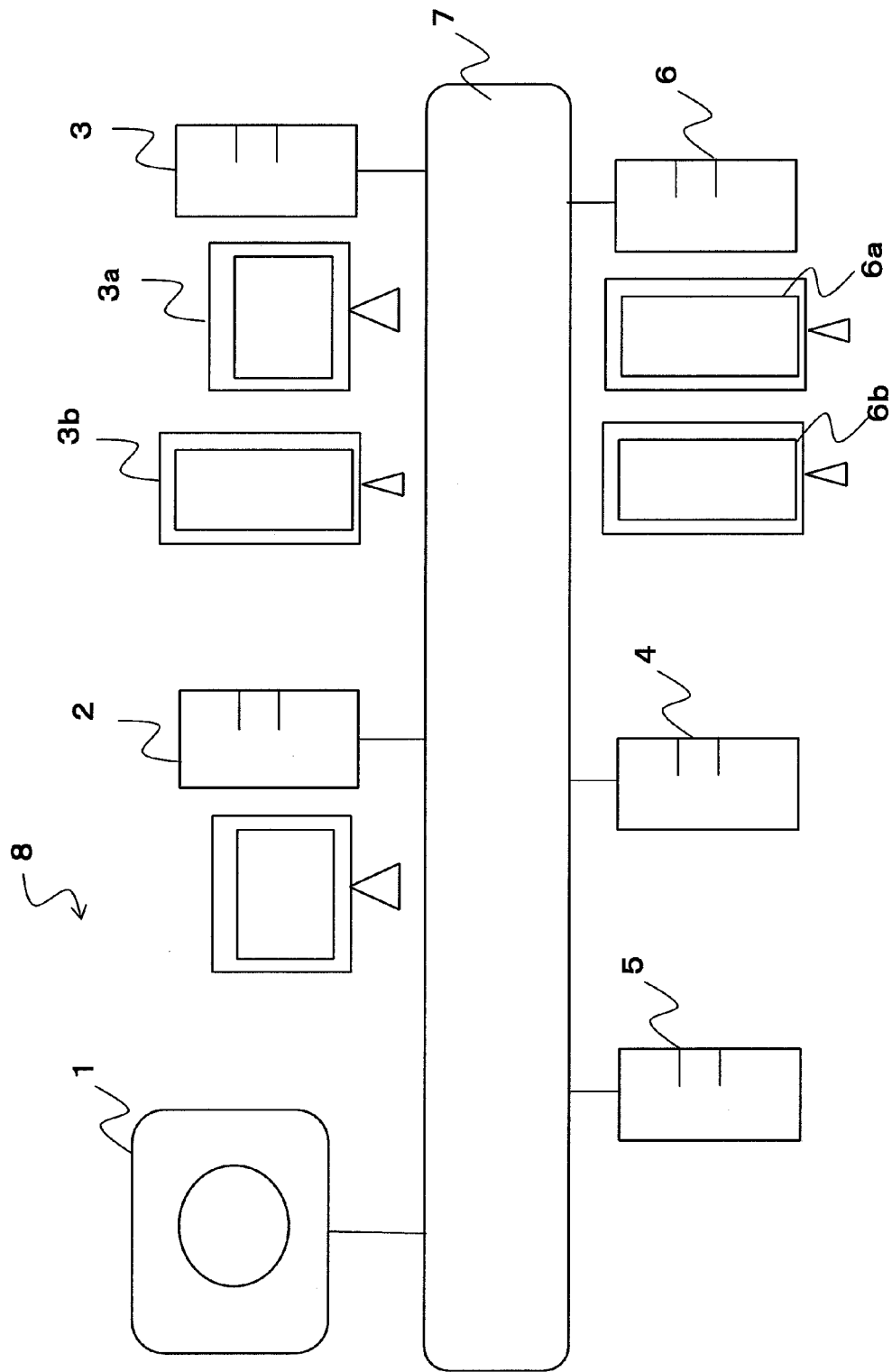
FIG. 1 is a block diagram showing the entire configuration of an examination information display system.

Hereinafter, embodiments of the present invention will be described with reference to the drawings. Configurations having the same function or procedures of the same processing content are denoted by the same reference numerals, and explanation thereof will not be repeated.

The present embodiment is an examination information display device and method of extracting and displaying the history of examination information of the same object and the examination information which is a candidate of comparative observation or comparative reference with a reference examination to be diagnosed.

In addition, the "examination information" includes medical images photographed by various medical image photographing apparatuses and examination data of various medical examinations, such as a blood test, a pathological examination, a biopsy, and an electrocardiogram.

In addition, it is also possible to include information subordinate to the examination, such as the letters of other hospitals or clinics.

First, an examination information display device (system) related to the present embodiment and the hardware configuration of the display device related to the present embodiment will be described on the basis of FIGS. 1 and 2.

Figure 2:
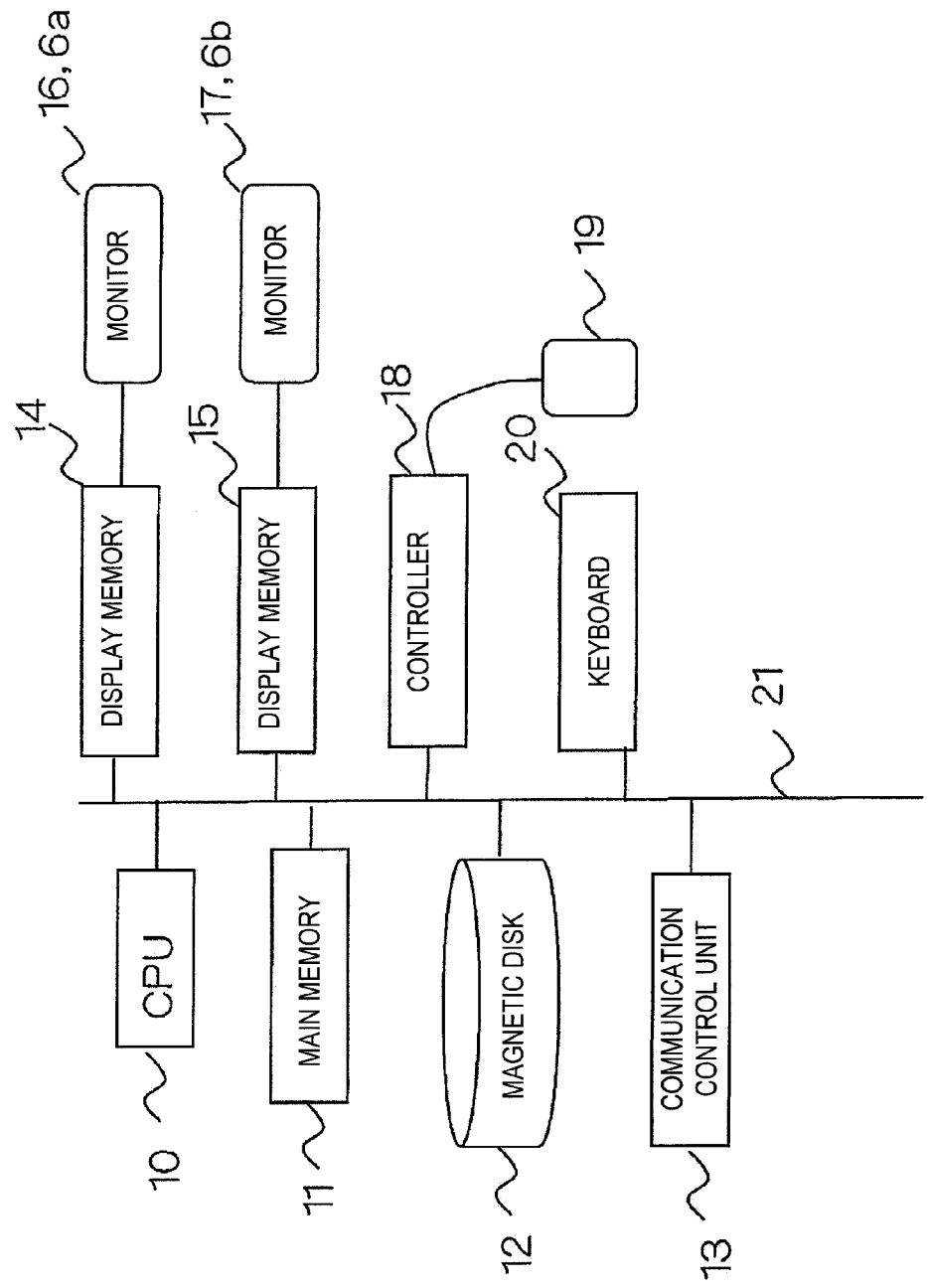
FIG. 2 is a block diagram showing the entire configuration of a display device.

FIG. 1 is a block diagram showing the entire configuration of the examination information display system related to the present embodiment. FIG. 2 is a block diagram showing the entire configuration of the display device related to the present embodiment.

An examination information display system 8 is a system configured such that a laboratory technician can photograph a patient or a person who has a medical examination (these are collectively an "object") to create a medical image and a radiologist or the like can conduct an inspection including interpretation for examination referring to the medical image. The examination information display system 8 is configured to include: a medical image capturing apparatus (also referred to as a "modality") 1; an image workstation 2; an image inspection terminal 3 which inspects a medical image and image display devices 3a and 3b connected to the image inspection terminal 3; an image server 4 in which medical images and the supplementary information are stored; an examination data server 5 in which a medical examination result and the supplementary information are stored; and a reading terminal 6 and image display devices 6a and 6b connected to the reading terminal 6, all of which are connected to one another through a network 7.

The modality 1 is a medical image capturing apparatus, such as an X-ray photographing apparatus, an X-ray CT apparatus, or an MRI apparatus, and photographs a predetermined portion of a patient to create a photographed medical image. The image workstation 2 creates a medical image by performing processing, such as three-dimensional (stereoscopic) image processing or Perfusion analysis (hereinafter, referred to as a post-processing medical image), on the basis of the photographed medical image created by the modality 1. The image inspection terminal 3 receives the photographed medical image from the modality 1 or the post-processing medical image from the image workstation 2 as a non-inspected medical image, and conducts an image inspection such as content check, modification, or processing of the non-inspected medical image. The image server 4 stores and manages the object information and the medical image inspected by the image inspection terminal 3 so as to be associated with each other.

The examination data server 5 stores and manages object information and examination result data of medical examinations, such as a blood test, an object body test, a biopsy, and an electrocardiogram, so as to be associated with each other. The reading terminal 6 is a terminal unit that acquires predetermined medical images or examination data from the image server 4 or the examination data server 5 and that is used when a radiologist performs interpretation or inspection referring to these medical images or examination data.

Here, the modality 1, the image workstation 2, and the image inspection terminal 3 are installed in a technician room and are used by a laboratory technician, and the reading terminal 6 is installed in a reading room of a radiologist in charge of interpretation and is used by the radiologist. In addition, only the reading terminal 6 may be busy.

The reading terminal 6 also includes two image display devices 6a and 6b. An examination list screen (refer to FIG. 5) or an examination data operation screen (refer to FIG. 6) is displayed on one image display device 6a, and a reference examination to be diagnosed or examination information, which is a candidate referred to or compared with the reference examination, is displayed on the other image display device 6b. In addition, although the reading terminal 6 includes two image display devices 6a and 6b in the present embodiment, the reading terminal 6 may be configured to include one or more image display devices, and the number of monitors is not limited to 2.

The image server 4 stores a medical image photographed by the modality 1 and supplementary information, which is added to the medical image, so as to be associated with each other. This supplementary information includes object information (for example, an ID for identification of an object, a name of an object, and a problem name including a disease name or a symptom name of an object), examination attribution information (for example, the type of modality, an examination date, and a photographed portion), and thumbnail images of a medical image. The examination attribution information is also called examination type information.

The examination data server 5 stores data of various medical examination results, such as a blood test, a tissue (examined body) examination, and electrocardiogram data, and information added to this data of examination results so as to be associated with each other. The supplementary information of the examination result data includes object information (for example, an ID for identification of an object, a name of an object, and a problem name including a disease name or a symptom name of an object) and examination attribution information (for example, the type of examination or an examination date).

Next, the hardware configuration of the reading terminal 6 as an examination information display device related to the present invention will be described on the basis of FIG. 2.

The reading terminal 6 is configured to include: a CPU 10 which controls each unit; a main memory 11 to which a control program required for the CPU 10 to perform overall control or various application programs for screen display and the like are loaded when these programs are executed; a magnetic disk 12 on which the above-described application software or medical images or examination data, which is acquired from the image server 4 and the examination data server 5, and data of the layouts of screens displayed on monitors 16 and 17 or data of object information, markers, tags, examination icons, and the like added to the layout are stored in a nonvolatile manner; a communication control unit 13 that is connected to the network 7 and performs communication control; display memories 14 and 15 which store image information for display temporarily; the monitor 16 which performs image display using the image information stored in the display memory 14; the monitor 17 which performs image display using the image information stored in the display memory 15; a controller 18 and a mouse 19 for operating the display screens of the monitors 16 and 17; and a keyboard 20 including operation keys and operation switches for setting various parameters, all of which are connected to one another through an internal bus 21. In addition, the main memory 11 has a function described in the magnetic disk 12. The control method of the CPU 10 is realized by each control program described below.

In addition, an external interface (not shown) for connecting an information device, such as a digital camera or a scanner, may be provided in the reading terminal 6. The reading terminal 6 may connect the external interface to a digital camera to acquire a photo of the lesion of a patient, which is taken in the department of dermatology, or may connect the external interface to a scanner to acquire associated materials. In addition, although the configuration in which the two monitors 16 and 17 are provided has been described herein as an example, only one monitor may be provided.

Here, the display memory 14 and the monitor 16 form the image display device 6a in FIG. 1, and the display memory 15 and the monitor 17 form the image display device 6b in FIG. 1. In addition, the examination icons are assumed to include not only icons but also a menu, a context menu, buttons, and a thumbnail display of examination images in a broad sense.

In addition, a touch panel may be provided on a display screen of each of the monitors 16 and 17. In this case, it is possible to input required data by the touch operation on the display screens of the monitors 16 and 17 instead of the mouse 19 or the keyboard 20. In addition, as information storage media, other storage media, such as a CD-ROM or a magneto-optical disc, may be used instead of the magnetic disk 12 or together with the magnetic disk 12.

Figure 3:
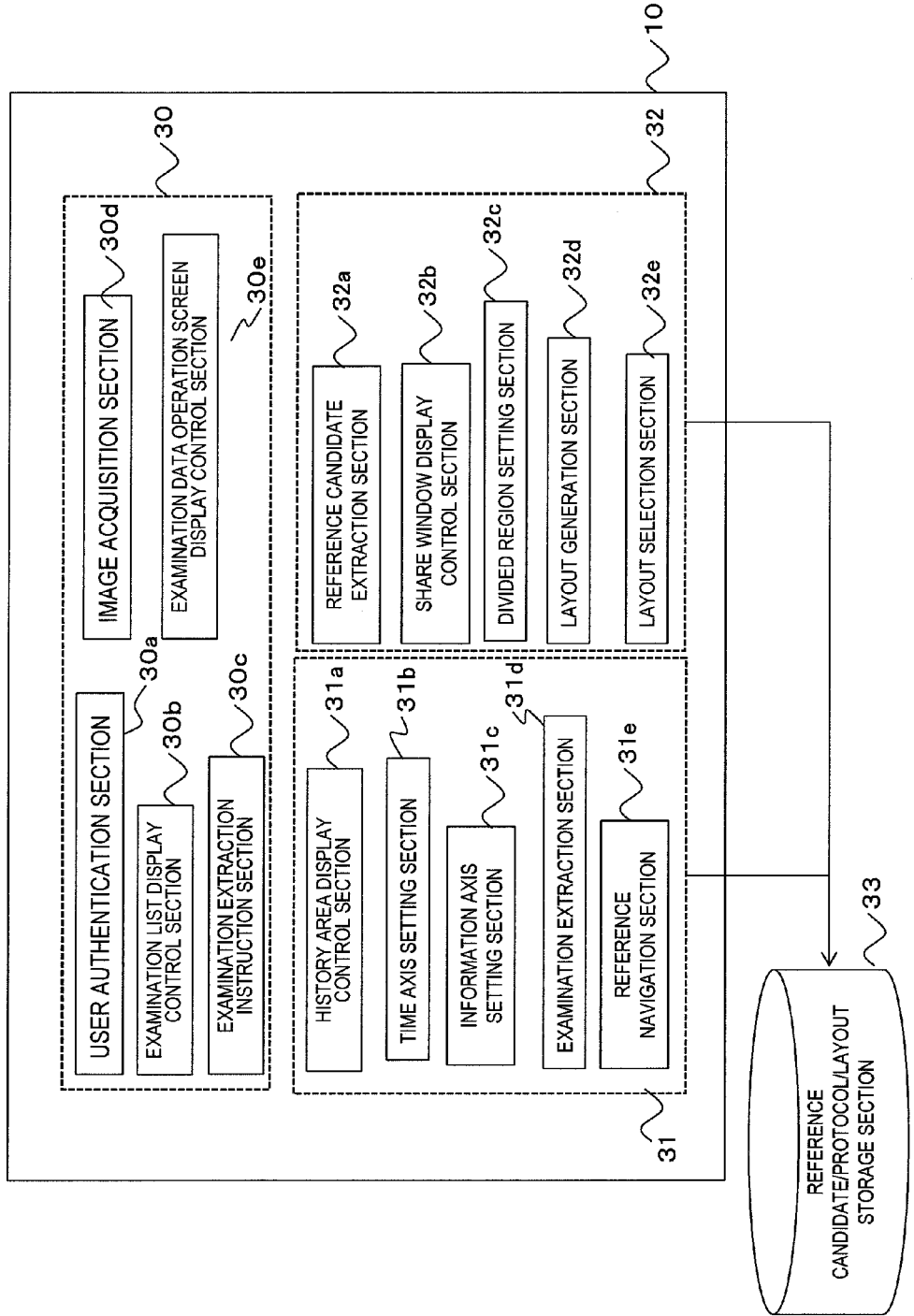
FIG. 3 is a block diagram showing an image display program.

Next, an image display program installed in the reading terminal 6 will be described on the basis of FIG. 3. FIG. 3 is a block diagram showing an image display program. The image display program includes largely a common program 30, a history area program 31 which controls a history area where the examination history of an object is displayed, and a share window program 32 which controls a share window in which examination information as a reference candidate is displayed.

The common program 30 includes: a user authentication section 30a which performs authentication processing on the basis of an input of a user ID for identification of a user of the reading terminal 6; an examination list display control section 30b which displays an examination list screen on which a medical image as a candidate of an object to be diagnosed or examination data of a medical examination (hereinafter, referred to as "examination data") is listed; an examination extraction instruction section 30c which selects a medical image or examination data (hereinafter, referred to as a "reference examination") as an object to be diagnosed on the examination list screen and instructs the image server 4 or the examination data server 5 to extract the reference examination and examination information of the same object as the reference examination; an image acquisition section 30d which acquires or receives the reference examination and the examination information extracted from the image server 4 or the examination data server 5; and an examination data operation screen display control section 30e which displays an examination data operation screen including the display area of the examination history and the display area of the examination information. The image server 4 and the examination data server 5 may be formed as one server. In this case, the examination data from the image server 4 and the examination data server 5 is centrally managed. Accordingly, if the search conditions are set for a medical image or examination data of a medical examination, it is possible to search for examination data as candidate examination information on the same date, for example.

The history area program 31 includes: a history area display control section 31a which arrays examination icons showing thumbnail images of a medical image and examination data in the examination history area (also referred to as a history area), in which the horizontal axis is a time axis indicating an examination date of a medical image and examination data and the vertical axis is an information axis indicating object attributes or examination attributes, on the screen of the image display device 6a; a time axis setting section 31b which sets the time axis indicating the time series of an examination date; an information axis setting section 31c which selects examination attributes and object attributes of the examination information and the reference examination and sets the information axis on the basis of the attributes; an examination extraction section 31d which extract thumbnail images or examination icons arrayed in the examination history area according to the disease name or the symptom of an object; and a reference navigation section 31e which displays the reference order of the examination information in the examination history area along the reference procedure corresponding to the user and the reference examination. Although an example where the time axis and the information axis are perpendicular to each other is described, both the axes are not limited to being perpendicular to each other, and may be parallel or at the twisted positions as long as the axes are separately provided. In addition, the area and the display region are synonymous.

When there are thumbnail images in the supplementary information of a medical image, the history area display control section 31a reads the thumbnail images and arrays the thumbnail images in the history area. When there is no thumbnail image in the supplementary information of a medical image, the history area display control section 31a generates thumbnail images of a medical image and arrays the thumbnail images in the history area. In addition, the history area display control section 31a arrays an examination icon showing the examination type of examination data in the history area.

In addition, when there is information which supports an operation (hereinafter, referred to as "reading support information") in image diagnosis of a user or on the examination data operation screen, the tag or mark indicating that there is reading support information is displayed together with the thumbnail images or the examination icon of the history area. For example, the reading support information described above is information indicating a reference examination, information indicating the number of overlapping examinations or a key examination in comparative reading and diagnosis of the reference examination when thumbnail images or an examination icon is overlap-displayed on the history area, and information indicating that a note (report) is attached to the examination.

The share window program 32 includes: a reference candidate extraction section 32a which extracts examination information as a reference candidate with respect to a reference image from the image server 4 and the examination data server 5; a share window display control section 32b which displays the extracted reference candidate in a share window that is a screen region of a different examination data operation screen from the history area; a divided region setting section 32c which sets a plurality of divided regions in the share window and determines the display position of examination information that is additionally displayed in each divided region; a layout generation section 32d which generates a display position pattern (layout) of the examination information in the share window; and a layout selection section 32e which selects an arbitrary layout. When the image server 4 and the examination data server 5 are formed as one server, the past examinations may be extracted from one server.

In addition, the main memory 11 or the magnetic disk 12 may include a reference candidate/protocol/layout storage section 33 which stores data that defines examination information as a reference candidate, which corresponds to identification information of a user, a routine name indicating the purpose of the diagnosis using a reference examination, and the examination type of the reference examination, along the order of comparative observation or the order of reading or reference (hereinafter, referred to as a "reference procedure" or a "reading protocol").

FIG. 4 is a view showing an example of data stored in the reference candidate/protocol/layout storage section 33. In this data, a user name, a routine name, and the examination type of a reference examination and a reference candidate and its reference procedure (protocol) corresponding to these are associated with each other. In addition, three layouts are set as display position patterns in the share window of the reference candidate. In addition, in each protocol, the user may write a comment showing the point of diagnosis in association with a reference candidate. This comment is used in the reference order display (reference navigation) which will be described later.

A user may set a reference candidate, a protocol, or a layout arbitrarily through a GUI (not shown), or the layout generation section 32d may generate a layout or the reference procedure automatically on the basis of the reference procedure or the layout of the reference candidate continuously recorded after login.

The share window display control section 32b displays a medical image or examination data as a reference candidate along the selected layout. In addition, when a new reference image is selected, a reference candidate corresponding to the new reference image is change-displayed in the share window. In addition, when a thumbnail image or an examination icon in the history area is dragged and dropped into the share window, screen splitting of the share window is performed, and an examination displayed according to the size of the split screen and an examination corresponding to the dragged and dropped thumbnail image or examination icon are adjusted in their screen sizes and displayed.

The above image display program is loaded to the main memory 11 of the reading terminal 6 and is executed by the CPU 10, thereby realizing the function in cooperation with hardware. Hereinafter, the flow of the process of the image display system related to the present embodiment will be described along each step in FIG. 5. FIG. 5 is a flow chart showing the flow of the process of the image display system. In the following process, the user who is a radiologist selects a medical image or examination data to diagnose (hereinafter, referred to as a "reference examination"), and displays the examination information of the same object as examination history in the history area and also displays examination information, which is a candidate referred to or read for comparison, in the share window.

Hereinafter, a case of making a diagnosis of colon cancer using a medical image (examination date: Jun. 6, 2009, modality: CT, examination portion: lower abdomen, routine name: colon cancer) of the object name "HITACHI A-RO" as a reference examination will be described as an example.

(Step 1)

When starting the operation of the reading terminal 6, the user (radiologist: assumed to be HITACHI Dr) inputs a user ID for identification of a user. The user authentication section 30a performs login processing using the user ID. A reference procedure storage section 31f starts processing of storing the user ID and the order of an examination that the user refers to in subsequent steps so as to be associated with each other (S1).

(Step 2)

Figure 6:
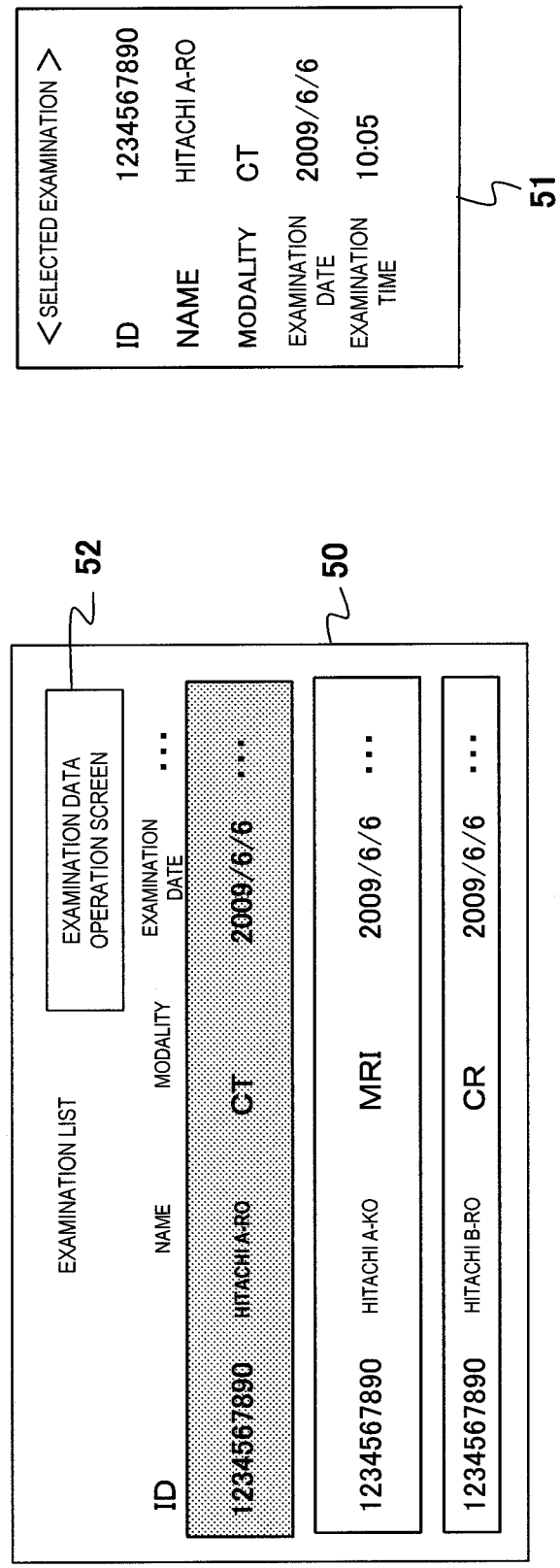
FIG. 6 is a schematic diagram showing an example of an examination list screen.

When the user gives an instruction to display the examination list screen by operating the mouse 19 or the keyboard 20 of the reading terminal 6 or by performing a touch operation on the display screen of the monitor 16, the examination list display control section 30b displays the examination list screen on the monitor 16 by reading the layout of the examination list screen from the main memory 11 or the magnetic disk 12 and transmitting it to the display memory 14. FIG. 6 is a schematic diagram showing an example of the examination list screen. An examination list screen 50 in FIG. 6 has fields of "(object) ID", "name", "modality", and "examination date". In addition, supplementary information of medical images photographed on the examination date "Jun. 6, 2009" is listed on the examination list screen 50.

(Step S3)

The user designates a record of an examination to diagnose on the examination list screen 50 using the mouse 19, the keyboard 20, or a touch panel (not shown). In FIG. 6, a "CT" image of "HITACHI A-RO" photographed on "Jun. 6, 2009" is selected. This selected "CT" image becomes a reference examination in the following process, and the detailed information is displayed on a detail screen 51 which is a different region from the examination list screen 50 of the monitor 16. After the end of selection, the user clicks on an "examination data operation screen" icon 52 provided on the examination list screen 50. In addition, although only medical images are described on the examination list screen 50 in FIG. 6, it is also possible to display a list of examination data with no image, such as a blood test or a biopsy.

(Step S4)

The examination extraction instruction section 30c sends instructions of search, extraction, and transmission of past examinations to the image server 4 and the examination data server 5 with the object (in the present embodiment, "HITACHI A-RO") of the reference image as extraction conditions. The image server 4 and the examination data server 5 extract each examination according to this instruction. For example, supplementary information including an ID for identification of the object, the name of the object, the type of modality, and examination date and time is added to each extracted examination. The image server 4 and the examination data server 5 transmit each examination and the supplementary information to the reading terminal 6 through the network 7. The image acquisition section 30d receives each examination and the supplementary information and stores them in the main memory 11 or the magnetic disk 12.

(Step S5)

Figure 7:
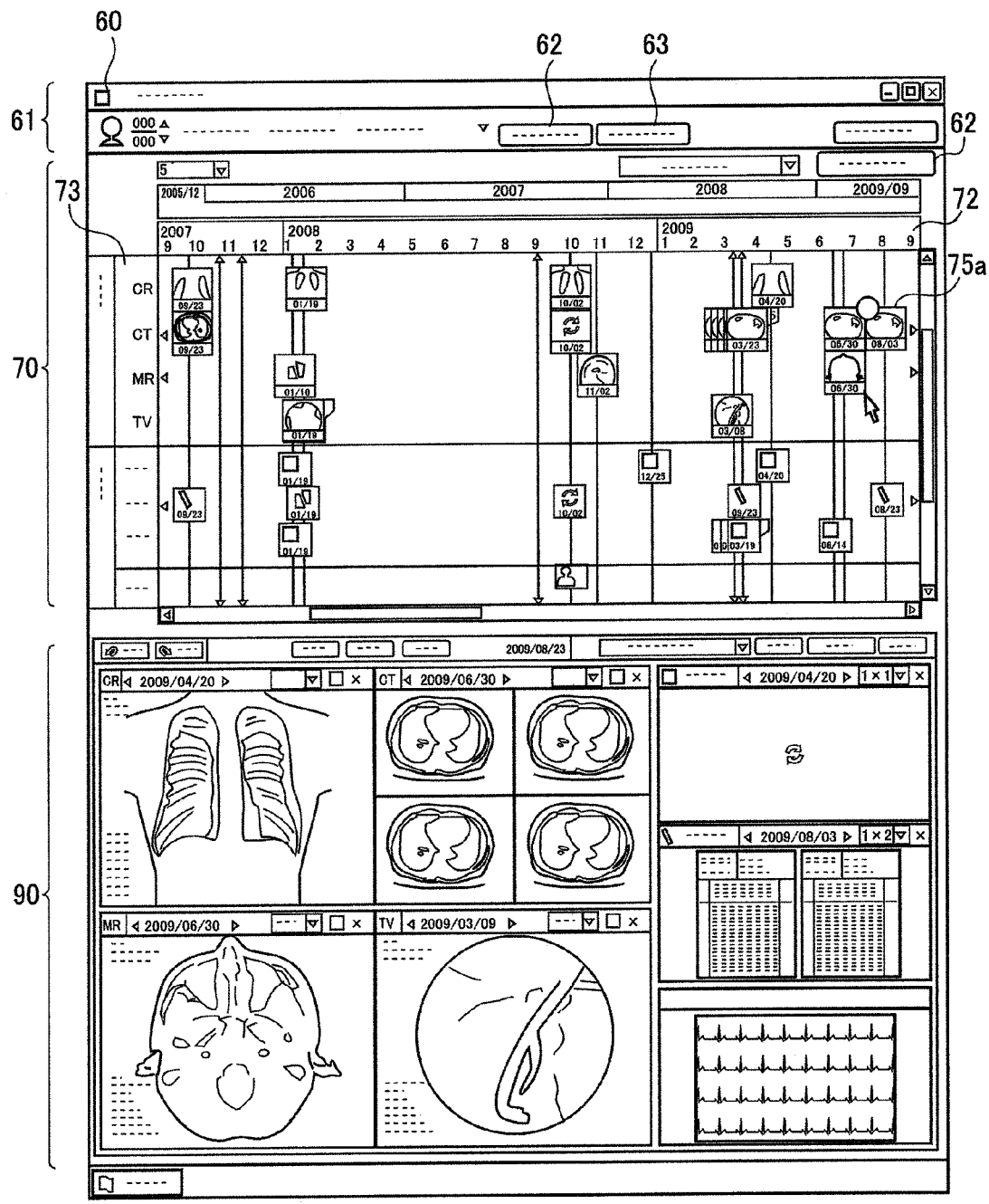
FIG. 7 is a schematic diagram showing an example of an examination data operation screen.

The examination data operation screen display control section 30e reads frames of the examination data operation screen from the main memory 11 or the magnetic disk 12, transmits the frames to the display memory 14, and displays the examination data operation screen 60 on the monitor 16. As a result, the display screen of the monitor 16 changes from the examination list screen 50 in step S2 to the examination data operation screen 60. FIG. 7 is a schematic diagram showing an example of the examination data operation screen. The examination data operation screen 60 is configured to include an object information area 61 where information that specifies an object is displayed, a history area 70 where the history of past examinations of an object is displayed, and a share window 90 where an examination as a reference candidate is displayed when diagnosing a reference image or reference examination data. The "object ID" and the "name" of the object of the reference image are displayed in the object information area 61. In addition, an image arrangement panel is displayed in the object information area 61. In FIG. 6, "HITACHI A-RO" selected in step S3 is displayed.

Display of the history area 70 is controlled by the history area program 31, and display of the share window 90 is controlled by the share window program 32. Hereinafter, the flow of the process of initial display of the history area will be described in steps S501 to S505, and the flow of initial display of the share window will be described in steps S511 to S513.

Figure 8:
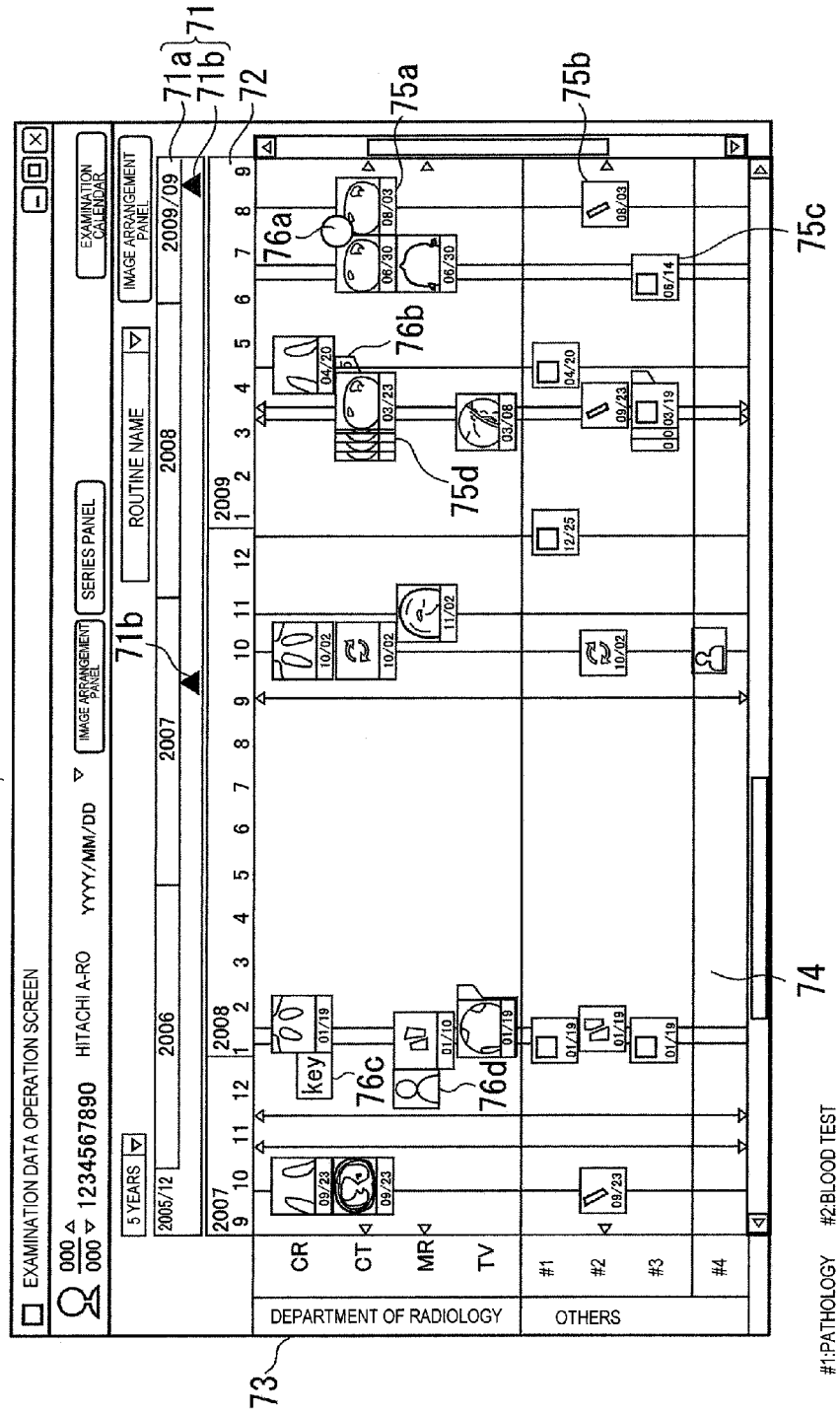
FIG. 8 is a schematic diagram in which a history area 70 included in an examination data operation screen 60 in FIG. 7 is displayed in an enlarged manner.

Hereinafter, the history area will be described on the basis of FIGS. 8 to 14. FIG. 8 is a schematic diagram in which the history area 70 included in the examination data operation screen 60 in FIG. 7 is displayed in an enlarged manner.

(Step S501)

The history area display control section 31a reads "examination date", "modality", and "examination type", which are included in the supplementary information of the examination information, from the main memory 11 or the magnetic disk 12. In addition, the history area display control section 31a transmits the reference image to the display memory 15 and displays the reference image on the monitor 17 (image display device 6b) (S501).

(Step S502)

The time axis setting section 31b and the information axis setting section 31c set the time axis 72 and the information axis 73 of the history area, respectively (S502).

The time axis setting section 31b reads the examination date included in the supplementary information read in step S501, and sets a period of an overhead area 71 of the history area 70 so that the entire history of past examinations of the object can be displayed. The overhead area 71 includes a time gauge 71a of the year display and two pointers 71b which designate an arbitrary point in time on the time gage 71a. When the user moves the pointer 71b in the horizontal direction in FIG. 8 using the mouse 19, the time axis setting section 31b sets the time axis 72 of the history area 70 according to the period designated by the two pointers 71b.

In addition, as an example of the setting of the time axis 72, when the user drags the mouse 19 left and right on the overhead area 71 while the left button of the mouse 19 is being clicked, a time domain of the time axis 72 moves while maintaining the time width. In addition, when the user drags the mouse 19 up and down, the examination type of a portion which could not be entered on the screen is referred to. When the user rotates the wheel of the mouse 19, the time width of the time axis 72 can be reduced or extended (S502).

In the initial display, a time range (December 2005 to September 2009) in which the entire examination history of the object can be displayed is set on the time axis 72. However, in order to refer to the detailed information of the reference examination Jun. 6, 2009, the time axis is changed by operation of the mouse 19, and the time axis 72 of the history area 70 is changed so that detailed examination information of the past two years can be displayed in general. Therefore, the two pointers 71b point out a period of September 2007 to September 2009 of the time gauge 71a, and this matches the time width of the time axis 72 in the history area 70. In addition, the time width of the time axis 72 may be changed by selecting the time axis 72 from the preset conditions (for example, a time width such as the last one year or the last one year and six months).

In addition, the information axis setting section 31c sets the information axis 73 of the history area 70. The information axis setting section 31c sets the information axis 73 based on the "examination type" in the initial setting. In the example shown in FIG. 8, on the information axis 73 defined by the "examination type", for example, classification of the first hierarchy into the department of radiology and others is performed, and second hierarchy classification of the "department of radiology" into CR, CT, MR, TV, and the like is performed. Similarly, second hierarchy classification of the "others" into pathology, a blood test, microbiology, and a biopsy is performed. The classification in FIG. 8 is just an example, and the present invention is not limited to this classification and the hierarchies of the classification.

(Step S503)

The history area display control section 31a calculates a corresponding position of each examination in an examination history display area 74, which is a two-dimensional area having the time axis 72 as a horizontal axis and the information axis 73 as a vertical axis, on the basis of the supplementary information read in step S501 and displays thumbnail images and examination icons corresponding to each examination, for example, a thumbnail image 75a added to the reference image and examination icons corresponding to the type of examination data (for example, an icon 75b showing a blood test and an examination icon 75c showing a microbiological test) in the examination history display area 74 to generate a history area (S503).

(Step S504)

The history area display control section 31a displays reading support information in the same manner as for the arrayed thumbnail images and examination icons (S504). As an example of the reading support information, for example, a "moon" mark 76a indicating a reference image is attached to the thumbnail image 75a.

In addition, when there is a plurality of examinations on consecutive different date and time and thumbnail images or examination icons are displayed so as to overlap each other in the examination history display area 74 due to limitations of the width of the time axis 72, a tab 76b in which a number indicating the number of overlapping examinations is described is added to thumbnail images 75d, or only parts of the thumbnail images 75d are displayed as to overlap each other.

In addition, as another example of the reading support information, it is possible to add a "Key" mark 76c indicating a key image in reading for comparison with a reference image or to add a note mark 76d indicating that there is a note about an examination.

(Step S505)

The history area display control section 31a transmits the history area 70 to the display memory 14 and displays history area 70 at the predetermined position in the examination data operation screen 60 (S505).

Figure 9:
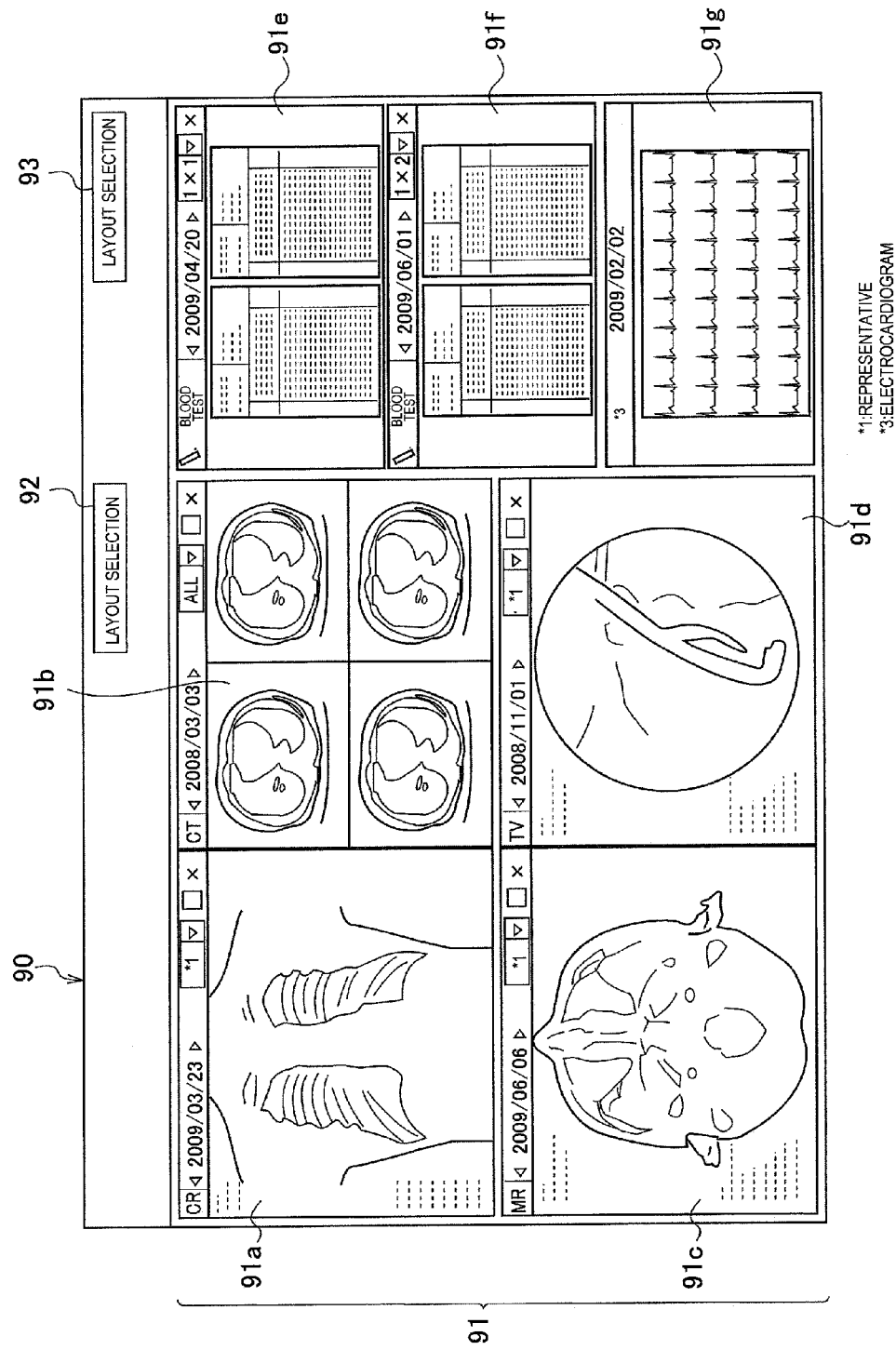
FIG. 9 is a schematic diagram in which a share window 90 included in the examination data operation screen 60 in FIG. 7 is displayed in an enlarged manner.

Hereinafter, the share window 90 is will be described on the basis of FIG. 9. FIG. 9 is a schematic diagram in which the share window 90 included in the examination data operation screen 60 in FIG. 7 is displayed in an enlarged manner. The share window 90 in FIG. 9 includes an examination area 91 where an examination is displayed, a "layout selection" button 92 for selecting the display position (hereinafter, referred to as a "layout") of each examination of the examination area 91, and a "layout registration" button 93 for registering a new layout. Functions of the "layout selection" button 92 and the "layout registration" button 93 will be described later in "display change 8: layout change of a share window".

Hereinafter, the flow of the process of displaying the initial screen of the share window 90 will be described along steps S511 to S513.

(Step S511)

According to the operation of the examination data operation screen in step S5, the reference candidate extraction section 32a reads the reference procedure corresponding to the examination type and a radiologist (in the initial setting, a user who has logged in step S1) from the reference candidate/protocol/layout storage section 33, and specifies an examination as a reference candidate according to the examination type of the reference examination. Then, a medical image or examination data of the specified examination as a reference candidate is read from the main memory 11 or the magnetic disk 12 (S511).

In the present embodiment, according to FIG. 4, seven reference candidates corresponding to a CT image of Jun. 6, 2009 as a reference image, that is, reference candidate 1: chest CR image 91a of Feb. 23, 2009, reference candidate 2: abdomen CT image 91b of Mar. 3, 2009, reference candidate 3: IVR perspective image (TV) 91d of the heart of Nov. 1, 2008, reference candidate 4: head MRI image 91c of Jun. 6, 2009, reference candidate 5: blood test data 91f of Jun. 1, 2009, reference candidate 6: biopsy data 91e of Apr. 20, 2009, and reference candidate 7: electrocardiogram of Feb. 2, 2009 are read.

(Step S512)

The share window display control section 32b reads the layout of the reference candidate corresponding to the user ID and the examination type of the reference image from the reference candidate/protocol/layout storage section 33 (S512). In the present embodiment, the layout 2 in FIG. 4 is read.

(Step S513)

The share window display control section 32b arrays the examination information as a reference candidate, which has been read in step S511, in the share window 90 of the examination data operation screen 60 along the layout read in step S512 (S513). As a result, examinations 91a to 91d are displayed in the share window 90.

(Step S6)

The user starts diagnosis in a state where the examination data operation screen (initial screen) 60 (FIG. 7) is displayed on the image display device 6a and the reference examination is displayed on the image display device 6b. In diagnosis of the reference examination, processing for display change of the history area 70 or processing for adding and deleting the reference candidate of the examination information displayed in the share window 90 is performed on the examination data operation screen 60 (S6).

Hereinafter, an example of display change of the history area 70 will be described in step S601, and an example of display change of the share window will be described in step S611. In addition, an example of display change when the history area and the share window are linked to each other will be described in step S621. Steps S601, S611, and S621 are executed when the user gives an instruction of each processing.

(Step S601)

When the user gives an instruction of the change of time axis, the change of information axis, extraction of examinations related to the specific disease name, or the like to the displayed history area, the processing is appropriately executed and the display of the history area is changed (S601). This processing is executed only when there is a display change instruction.

Display Change 1: Change of Time Axis

Figure 10:
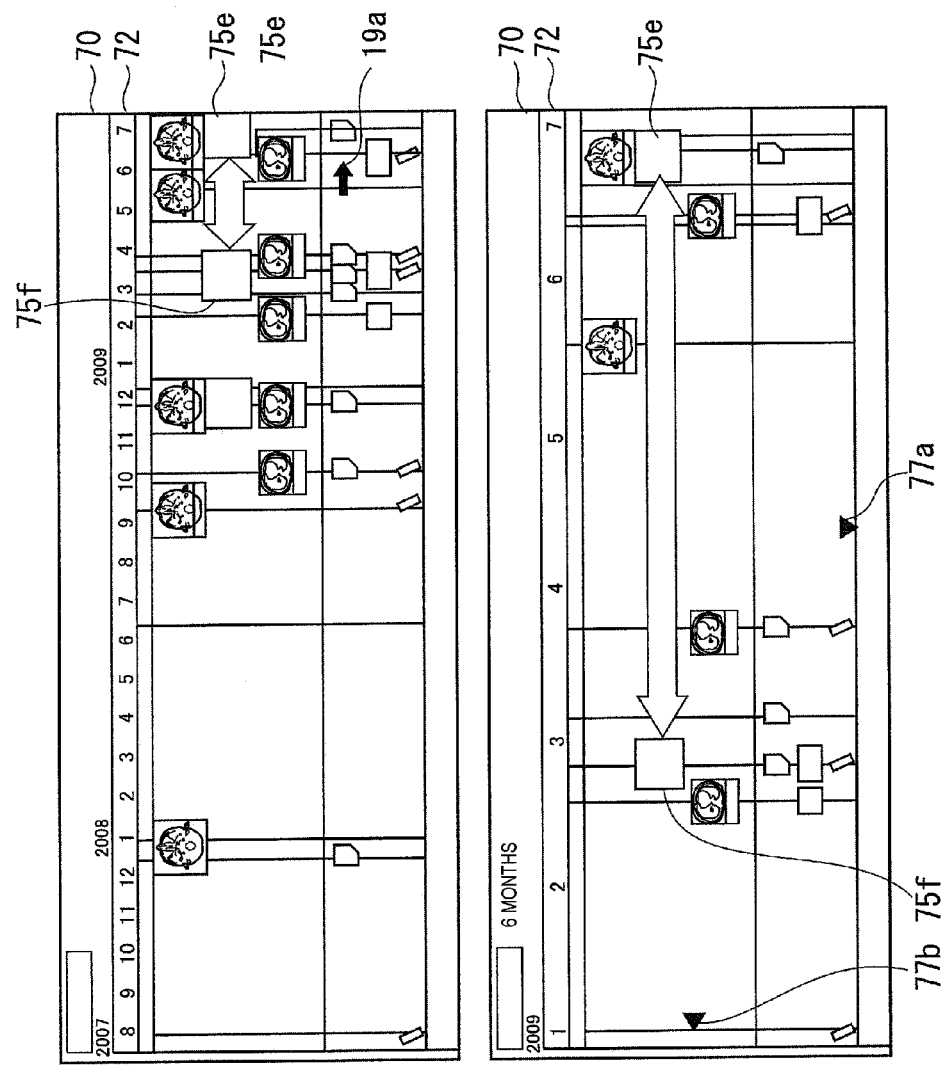
FIG. 10 is a schematic diagram showing a comparison between the history area before the change of time scale and the history area after the change of time scale.

The change of time axis will be described on the basis of FIG. 10. FIG. 10 is a schematic diagram showing a comparison between the history area before the change of time scale and the history area after the change of time scale.

Although the entire examination history of the object of the reference image is displayed in the initial display state, the time axis 72 may be changed by mouse operation in order to refer to the detailed information of the last examination. For example, when the user rolls the wheel of the mouse 19 in a state where a mouse cursor 19a is located in the history area 70 of the initial display in FIG. 10, the time width of the time axis 72 is changed according to the amount of wheel rolling with a mouse cursor portion as a newest examination and examination information of a desired period, for example, last six months from the examination date of the reference image is displayed in detail. In addition, instead of setting the mouse cursor portion as a newest examination, it is possible to extend or reduce the time width with the display position of the mouse cursor portion as the center. In addition, when the last six months is selected, the examination date of the selected examination may be set as a reference regardless of the position of the mouse cursor.

The history area 70a in FIG. 10 is formed when the time axis setting section 32 sets the time axis newly in response to the above-described mouse operation and the history area display control section 31a rearranges thumbnail images and examination icons in the examination history display area 74 according to the new time axis. Compared with the history area 70, the distance between thumbnail images 75e and 75f is increased and the last examination can be displayed in detail accordingly.

Display Change 2: Notice Outside the Area

When the time width of the time axis 72 is extended as in the display change 1, it may be difficult to grasp that there is an examination outside the examination history display area 74. Therefore, when there is examination information outside the examination history display area 74 of the history area 70, the history area display control section 31a displays a down (▼) mark 77a and a left (leftward triangle) mark 77b at the end of a table in order to remind the operator of it (refer to FIG. 10). Accordingly, the user can notice that there is an examination outside the examination history display area 74. When the user moves a display region vertically and horizontally in order to check which examination is present outside the shown range, the history area display control section 31a change-displays the examination information outside the examination history display area 74 in the examination history display area 74 according to the operation. Although not explained, only the arrow direction of an up mark or a right mark is opposite to that described above. Accordingly, except that the operation direction is opposite, an examination can similarly be checked by each operation of the mark.

Display Change 3: List Display of Overlapping Examinations

Figure 11:
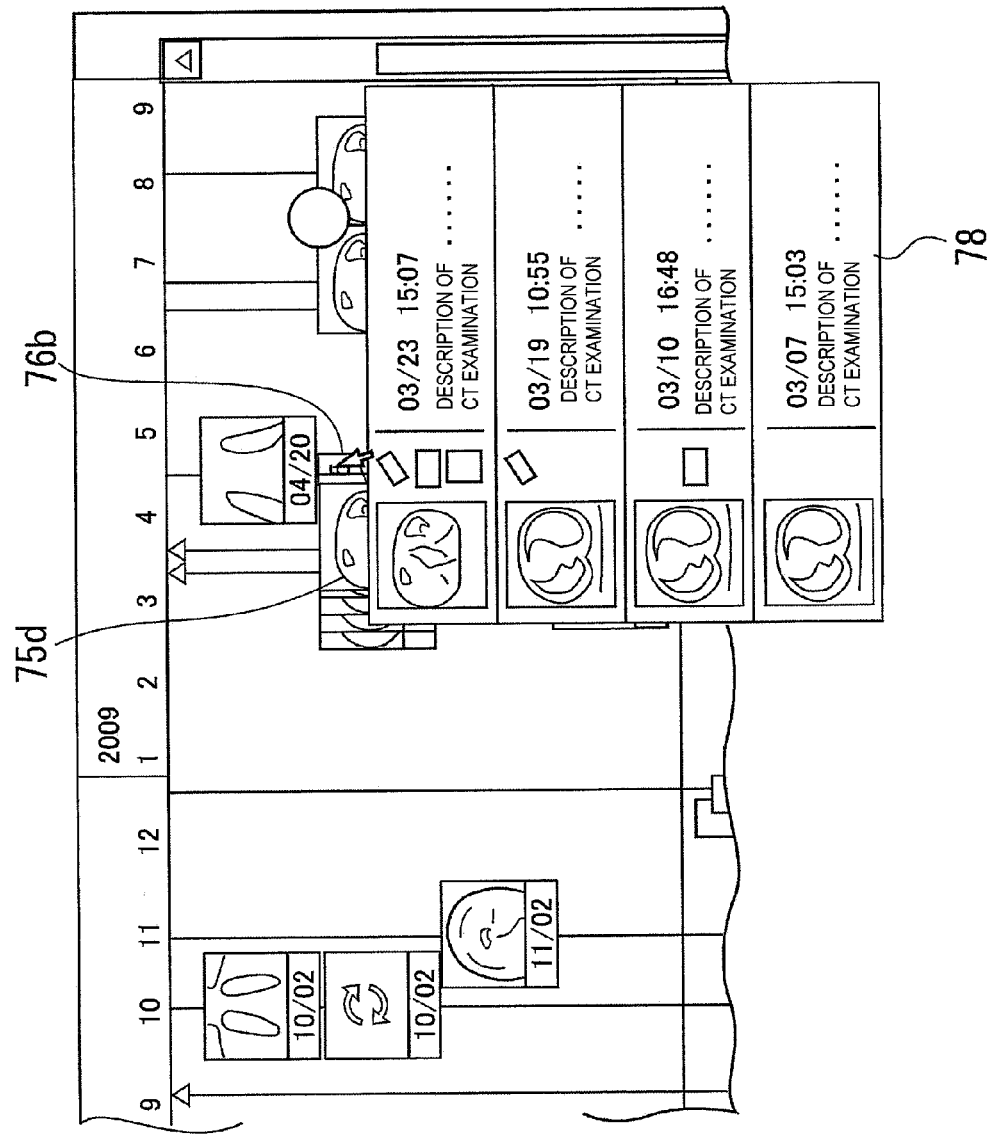
FIG. 11 is a schematic diagram showing a screen display example in which overlapping examinations are listed.

List display of overlapping examinations will be described on the basis of FIG. 11. FIG. 11 is a schematic diagram showing an example of screen display in which overlapping examinations are listed, and is an enlarged view of a portion around the thumbnail image 75d in FIG. 8.

The number of overlapping examinations "5" is displayed on the tab 76b attached to the thumbnail image 75b in FIG. 11. When the user clicks the tab 76b, the history area display control section 31a displays overlapping thumbnail images and supplementary information as a list 78. Although four thumbnail images are displayed in the list 78, these images are located behind the thumbnail image 75d which is overlap-displayed. In this manner, it is possible to check the thumbnail images and the supplementary information which are hidden behind the foremost surface due to overlapping display. In addition, the thumbnail image 75d of the foremost surface may also be included in the list 78. In addition, although thumbnail images have been described as an example in FIG. 11, examination icons may also be listed as described above even if the examination icons are displayed so as to overlap each other.

Display Change 4: Change of Information Axis

Figure 12:
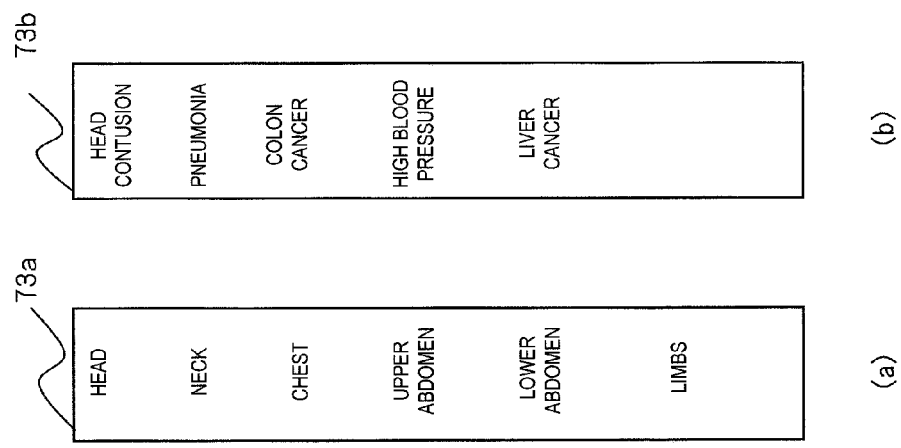
FIG. 12 is a schematic diagram illustrating a variation on the information axis.

List display of overlapping examinations will be described on the basis of FIG. 12. FIG. 12 is a schematic diagram illustrating a variation on the information axis.

When the user right-clicks after moving a cursor of the mouse 19 on the information axis 73 of the history area 70, attribute candidates which can be designated as the information axis are pull-down displayed. Here, when the user selects an "examination portion" as a desired attribute, the information axis setting section 31c changes the information axis 73 of the history area 70 to an information axis 73a defined by the "examination portion" in FIG. 12(a). On the information axis 73a, attributes of head, chest, abdomen, and limbs are arranged from above, similar to the arrangement of the human body. The history area display control section 31a redefines the examination history display area 74 with the information axis 73a defined newly, and rearranges thumbnail images and examination icons.

According to the information axis 73a based on the "examination portion", it becomes easy to refer to an examination of the same portion as an examination under diagnosis (reference image or reference examination data). For example, since both a thumbnail image of a CT image after ECG photographing and an examination icon showing electrocardiogram data are displayed at the position of the chest of the history area 70, cross reference of the CT image after ECG photographing and the electrocardiogram data becomes easy.

Here, when the user selects "disease names and problems" from the pull-down menu of attribute candidates, the information axis setting section 31c changes the information axis 73 of the history area 70 to an information axis 73b defined by the "disease names and problems" in FIG. 12(b). The information axis 73b is changed to "head contusion", "pneumonia", "colon cancer", "high blood pressure", and "liver cancer" from above. For these disease names and problems, those in active or follow states among the disease names and problems included in the supplementary information of the object of the reference image are preferentially displayed at the high location. Alternatively, the information axis setting section 31c may display the disease names and problems in descending order of importance referring to the importance data of disease names and problems (data in which disease names, problems, and their importance levels are matched to each other) stored in the main memory 11 or the magnetic disk 12 in advance. In addition, the disease names and problems, such as "head contusion" and "pneumonia", are just examples, and are not limited to these examples.

According to the information axis 73b based on the "disease names and problems", for example, both a thumbnail image of an MRI image of the head and an examination icon showing electrocardiogram data are displayed at the position of "head contusion" of the history area 70, cross reference when there is a plurality of examination results for the same disease name and problem becomes easy.

Figure 13:
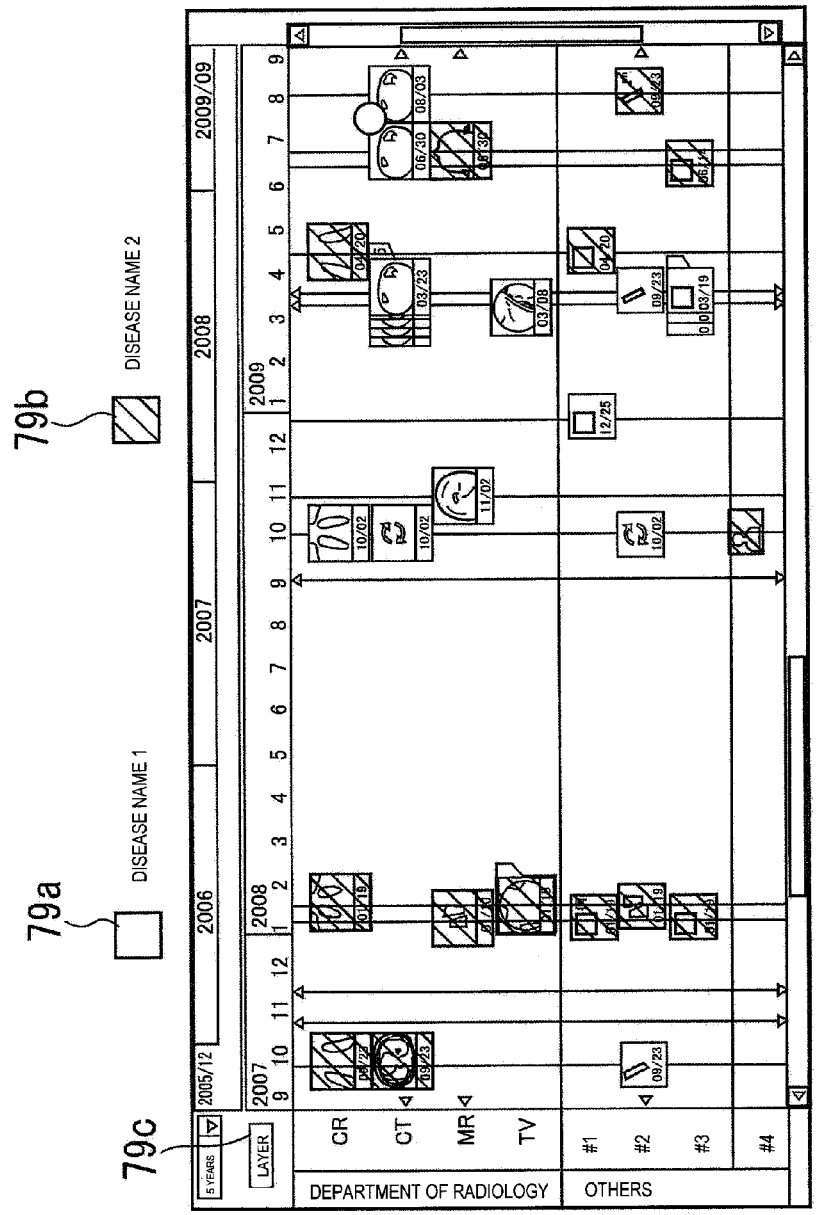
FIG. 13 is a schematic diagram showing an example in which the display mode of an examination has been changed according to the disease name.
Figure 14:
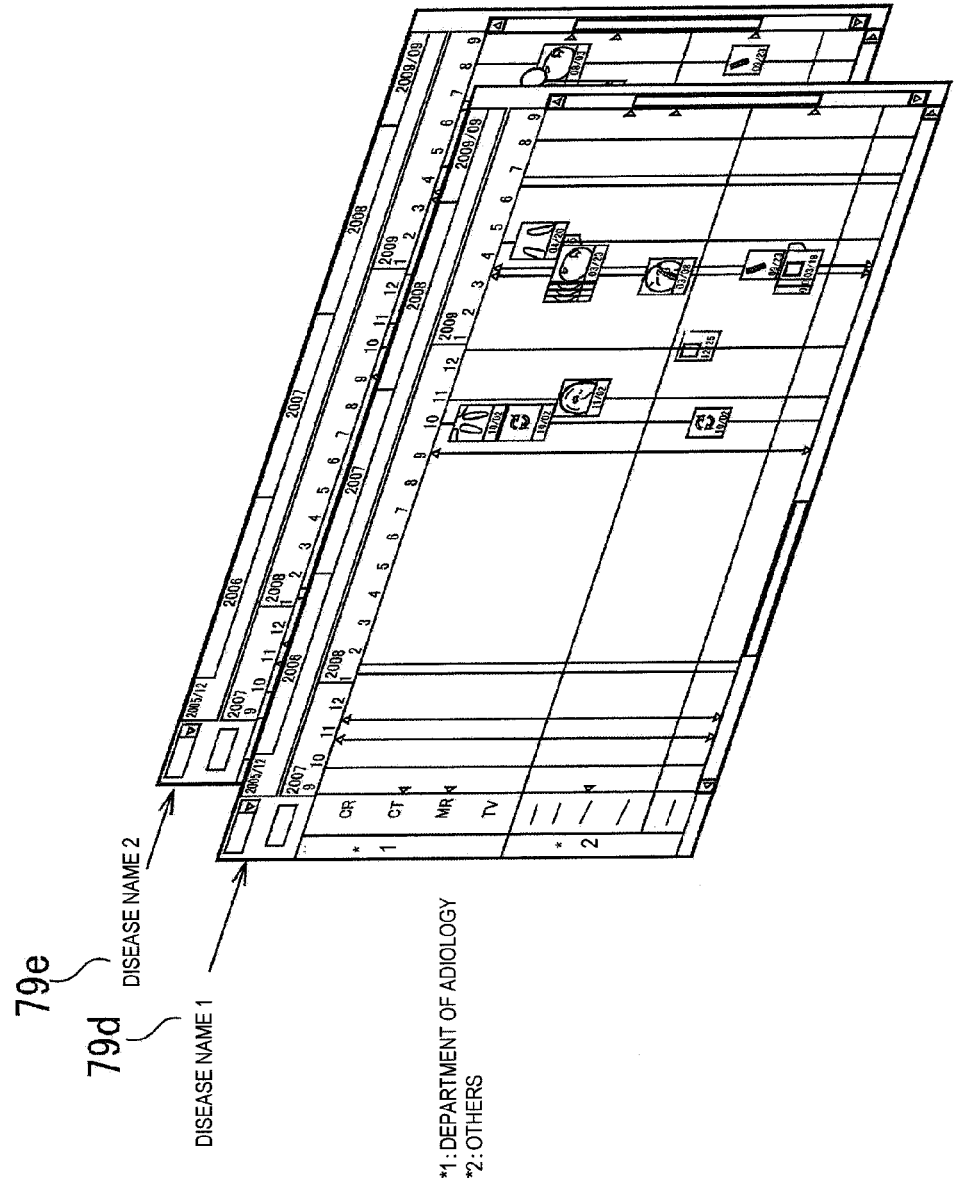
FIG. 14 is a schematic diagram showing an example in which the display mode of an examination has been changed according to the disease name.

Display Change 5: Extraction and Display of an Examination According to Each Disease Name and Problem List display of overlapping examinations will be described on the basis of FIGS. 13 and 14. FIG. 13 is a schematic diagram showing an example in which the display mode of an examination is changed according to each disease name, which shows an example in which the display mode is changed according to each disease name in the history area. FIG. 14 is a schematic diagram showing an example in which the display mode of an examination is changed according to each disease name, which shows an example in which an examination of one object is displayed by changing layers according to disease names and displaying the layers so as to overlap each other.

In order to check what kind of diagnosis the object has received until now and what kind of examination the object has received, the user moves a mouse cursor in the examination history display area 74 and right-clicks to select "disease names". When the "disease names" are selected, the examination extraction section 31e reads an object and supplementary information of an examination and displays a disease name candidate list with a pull-down menu (not shown). Here, when the user selects an arbitrary disease name, for example, "disease name 1", the examination extraction section 31d classifies examinations according to the disease name and performs grouping with reference to the disease name column of supplementary information of medical images and examination data. Then, as shown in FIG. 13, the history area display control section 31a changes a display mode according to each disease name and displays the thumbnail images and the examination icons. In FIG. 13, thumbnail images and an examination icon 79a showing an examination regarding the selected "disease name 1" are displayed with higher brightness than thumbnail images and an examination icon 79b of an examination of "disease name 2" which has not been selected.

In addition, when the user clicks a "layer" button 79c in the history area 70, the history area display control section 31a performs layer display of examinations classified by the examination type extraction section 31d as shown in FIG. 14. Only thumbnail images and examination icons of an examination regarding the disease name 1 are displayed on a layer 79d in FIG. 14, and only thumbnail images and examination icons of an examination regarding the disease name 2 are displayed on a layer 79e. When the layer 79e is clicked, the layer 79e is displayed on the front and the layer 79d is displayed on the back.

By presenting the user with examinations classified according to disease names, the user can easily check the history of diagnosis and examinations regarding a certain disease name.

Display Change 6: Reference Navigation Function

Figure 15:
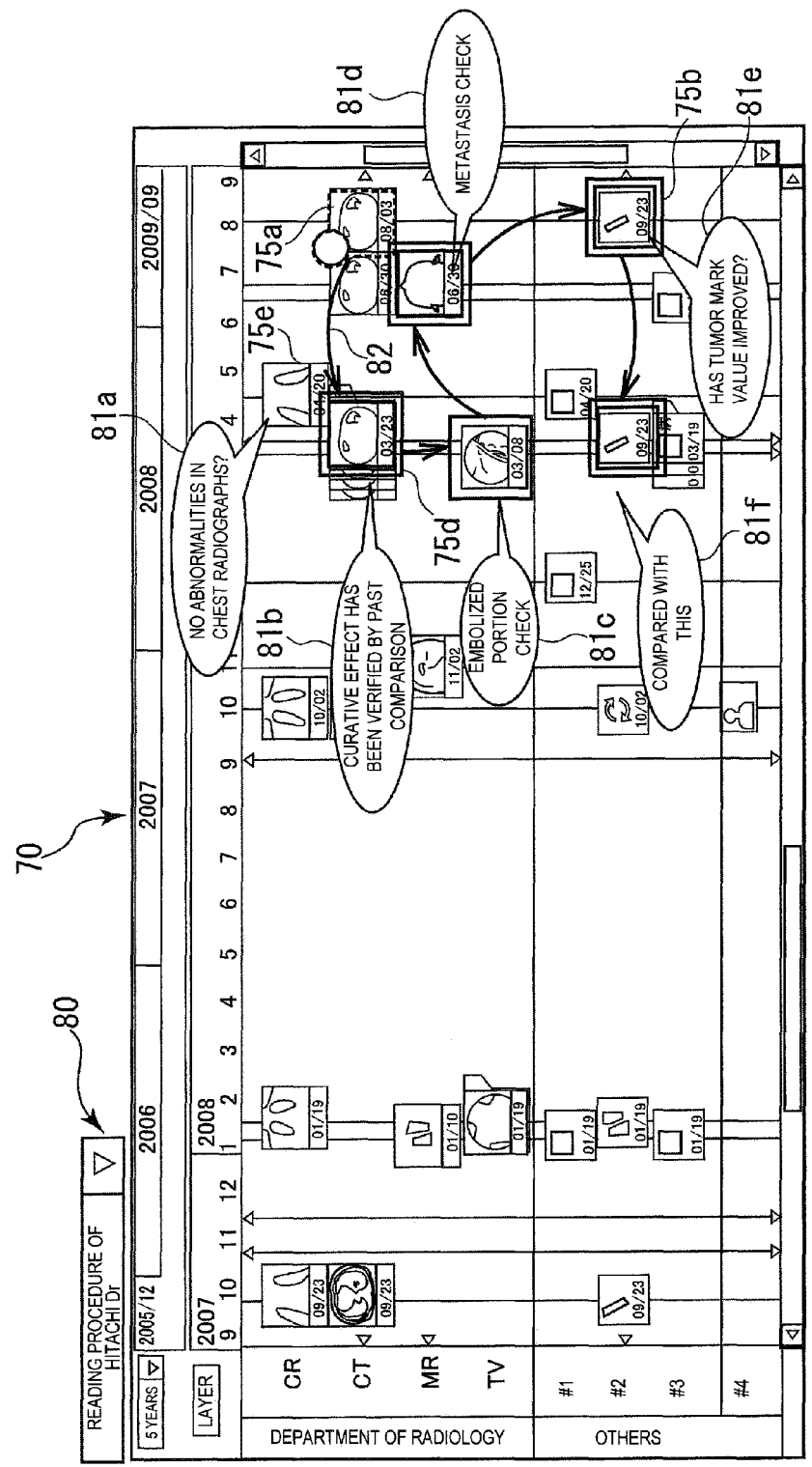
FIG. 15 is a schematic diagram showing a display example of reference navigation.

A reference navigation function will be described on the basis of FIG. 15. FIG. 15 is a schematic diagram showing a display example of reference navigation. A reference navigation icon 80 in the history area 70 is an icon for selecting the examination information reference procedure of each radiologist. After logging in to the reading terminal 6 through user authentication in step S1, the reference procedure storage section 31*f* stores the user ID and the examination order referred to by the user for comparison with the reference image.

Here, when a reading procedure selection button 80 is clicked to select an arbitrary radiologist, for example, when the "reading procedure of HITACHI Dr" is selected, the reference navigation section 31*e* searches for the data in the reference candidate/protocol/layout storage section 33 and reads a reference procedure when HITACHI Dr reads the reference image (in the present embodiment, a CT image). In addition, the examination information is indicated by arrows along the reference procedure. In addition, the reference navigation section 31*e* performs popup display of the comment, which is included in the data in FIG. 4, next to a thumbnail image or an examination icon. In the example shown in FIG. 15, referring to an examination of a thumbnail image 75*e* next is displayed by the arrow 82 with the thumbnail image 75*a* of the reference image as a starting point. A check point when reading the thumbnail image 75*e* is shown in popup display of "no abnormalities in chest radiographs?" 81*a*. Then, in the examination of the thumbnail image 75*d*, "curative effect has been verified by past comparison" 81*b* is displayed as a popup. Then, the procedure when HITACHI Dr reads a CT image regarding the disease name and the examination type of the reference image, for example, colon cancer is similarly displayed in the history area 70 by the arrow 82 and popup displays 81*c*, 81*d*, 81*e*, and 81*f*.

By this reference navigation function, the relationship between examinations displayed in the history area 70 can be seen along the reference procedure. In addition, by referring to the reading procedure of an arbitrary user, the user can make a diagnosis along the reference procedure and the reference point of a highly experienced radiologist, for example. Therefore, training effects of the radiologist can also be expected.

(Step S611)

When the user gives, for the share window 90, an instruction of addition and deletion of displayed medical images and examination data and an instruction to change the layout, the share window display control section 32*b* changes the display of the share window according to the operation (S611). This processing is executed only when there is a display change instruction.

Display Change 7: Addition and Deletion of a Reference Candidate

When the user designates a thumbnail image or an examination icon displayed in the history area 70 using the mouse 19 and drags and drops it to the share window 90, a medical image or examination data corresponding to the thumbnail image or the examination icon, which has been dragged and dropped, is additionally displayed at the dropped position. In addition, a medical image and examination data which have been displayed before the addition are reduced to make a region where the added examination is displayed, and the reduced image is displayed again in the share window 90.

On the other hand, when the user designates a medical image or examination data displayed in the share window 90 using the mouse 19 and right-clicks to select "delete" from the pull-down menu (not shown), the selected medical image or examination data is deleted, and the remaining medical image or examination data displayed in the share window 90 is enlarged according to the free space generated due to the deletion and the enlarged image is displayed again in the share window 90.

In this manner, examination information that the user wants to refer to appropriately is additionally displayed for the examination information displayed as a reference candidate of a reference image or reference examination data, or examination information which does not need to be referred to is deleted from the share window 90. As a result, since the remaining examination information displayed in the share window 90 is displayed on the larger screen, it is possible to improve the visibility.

The divided region setting section 32*c* divides the share window 90 into a plurality of regions. The divided regions are set in units of a medical image or examination data displayed in the share window 90. That is, a plurality of divided regions are set for each region where each medical image displayed in the share window 90 is displayed. In addition, for each divided region, the divided region setting section 32*c* sets the display position of a reference candidate whose additional display has been instructed by the drag and drop operation. Although the division pattern by the divided region setting section 32*c* is not limited to the following example, it is preferable that each medical image and examination data displayed in the share window 90 after the reference candidate is added have a rectangular shape.

Figure 16:
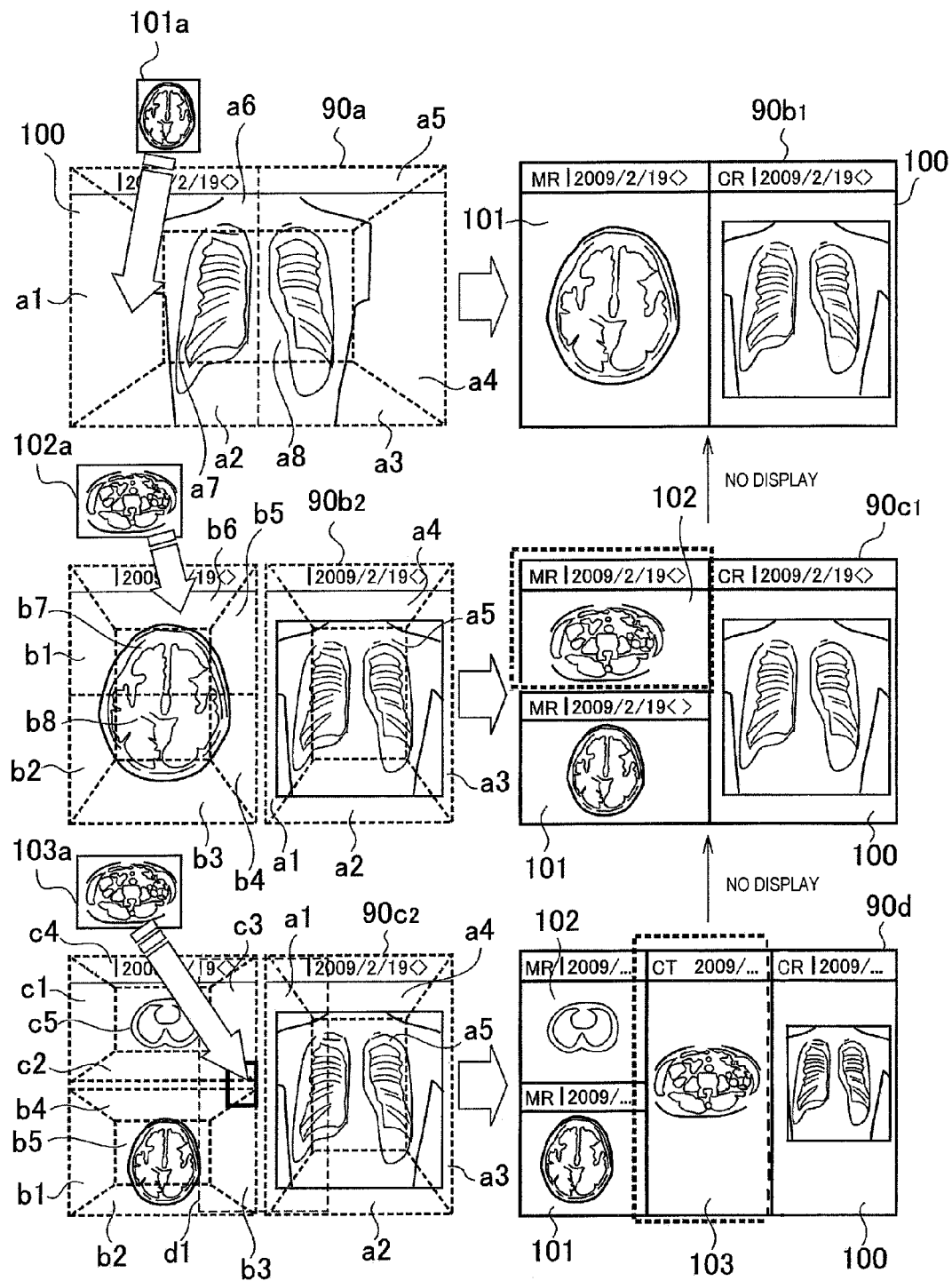
FIG. 16 is an explanatory view illustrating a transition of a share window according to addition and deletion of a reference candidate.

Hereinafter, processing of adding and deleting the examination information, which is to be referred to, to and from the share window 90 will be described on the basis of FIG. 16. FIG. 16 is an explanatory view illustrating a transition of the share window according to addition and deletion of a reference candidate. In FIG. 16, dotted lines of share windows 90*a*1, 90*b*1, and 90*c*1 indicate the borderlines of divided regions which will be described later. In addition, rectangular frames of share windows 90*b*2 and 90*c*2 displayed in dotes lines indicate reference candidates to be deleted.

For example, in the share window 90*a* in a first state where one medical image 100 is displayed, the divided region setting section 32*c* divides a region (equivalent to the full screen of the share window 90*a*1) where the medical image 100 is displayed into eight parts by diagonal lines, a rectangle including the point of intersection of the diagonal lines (including a rectangle and a square), and a vertical line which divides the share window 90*a*1 into two parts in a horizontal direction. In FIG. 16, a1 to a8 are equivalent to the respective eight divided regions. a1 is a left end region of the share window 90*a*, a2 is a lower left region of the share window 90*a*, a3 is a lower right region of the share window 90*a*, a4 is a right end region of the share window 90*a*, a5 is an upper right region of the share window 90*a*, a6 is a upper and left region of the share window 90*a*, a7 is a left middle region of the share window 90*a*, and a8 is a right middle region of the share window 90*a*.

In addition, as the display position of an added reference candidate, the left side of the medical image 100 (medical image 100 is equivalent to a reference candidate displayed on a1 before addition) is set for a1, the lower side of the medical image 100 is set for a2 and a3, the right side of the medical image 100 is set for a4, the upper side of the medical image 100 is set for a5 and a6, the left side of the medical image 100 is set for a7, and the right side of the medical image 100 is set for a8.

Here, when the user drags and drops a thumbnail image 101*a* displayed in the history area into the a1 region of the share window 90*a*1, the share window display control section 32*b* displays a medical image 101 corresponding to the thumbnail image 101*a* on the left side of the medical image 100 on the basis of the display position of the added reference candidate set in the a1 region. In this case, the share window display control section 32*b* calculates the number of medical images and examination data displayed in the share window 90*a* and performs screen splitting of the share window 90*a* using a number obtained by adding 1 (the number of added reference candidates) to the calculated number, that is, 2. In this screen splitting, since displaying the medical image 101 on the left side of the medical image 100 is already set by data corresponding to a1, the share window 90*a* is divided into two equal parts in the horizontal direction in FIG. 16. In addition, the image sizes of the medical images 100 and 101 are adjusted so as to match the screen size of each split screen, and the medical image 101 is displayed on the left split screen and the medical image 100 is displayed on the right split screen. As a result, the share window 90*a* changes to the share window 90*b*1.

The divided region setting section 32*c* sets divided regions again in the share window 90*b*1. The share window 90*b*2 is a view in which the borderlines of the divided regions set in the share window 90*b*1 are drawn by dotted lines. In the share window 90*b*2, the medical image 101, that is, a region (equivalent to the left screen of the share window 90*b*) where the medical image 101 is displayed is divided into eight parts by diagonal lines, a rectangle including the point of intersection of the diagonal lines (including a rectangle and a square), and a horizontal line which divides the medical image 101 into two parts in a vertical direction. In FIG. 16, b1 to b8 are equivalent to the respective eight divided regions. b1 is an upper left region of the display region of the medical image 101, b2 is a lower left region of the display region of the medical image 101, b3 is a lower region of the medical image 101, b4 is a lower right region of the medical image 101, b5 is an upper right region of the medical image 101, b6 is an upper region of the medical image 101, b7 is an upper middle region of the medical image 101, and b8 is a lower middle region of the medical image 101.

In addition, the divided region setting section 32*c* sets the display position of an additional examination next to the left side of the medical image 101 for b1 and b2, next to the lower side of the medical image 101 for b3 and b8, next to the right side of the medical image 101 for b4 and b5, and next to the upper side of the medical image 101 for b6 and b7. Also for the medical image 100, divided regions a1 to a8 equivalent to b1 to b8 are set again. The divided region setting section 32*c* sets the display position of an additional examination next to the right side of the medical image 100 for a1 and a2, next to the lower side of the medical image 100 for a3 and a8, next to the right side of the medical image 100 for a4 and a5, and next to the upper side of the medical image 100 for a6 and a7.

Therefore, when a thumbnail image 102*a* is dropped and dragged into b6, the share window display control section 32*b* displays a medical image 102 for the thumbnail image 102*a* additionally at the display position set for b6, that is, next to the upper side of the medical image 101. In order to perform this additional display, the share window display control section 32*b* divides the screen where the medical image 101 is displayed into two parts in the vertical direction, and adjusts the screen sizes of the medical images 101 and 102 such that the medical images 101 and 102 fit the divided upper and lower screens and displays the medical images 101 and 102. As a result, the share window 90*b*1 changes to the share window 90*c*1.

As described above, also for the share window 90*c*1, the divided region setting section 32*c* sets five divided regions of a1, b1, c1 (left region), a2, b2, c2 (lower region), a3, b3, c3 (right region), a4, b4, c4 (upper region), a5, b5, and c5 (middle region) for each of the medical images 100, 101, and 102. In addition, the divided region setting section 32*c* sets the divided regions such that an examination added to a1, b1, and c1 is displayed next to the left side of each medical image, an examination added to a2, b2, and c2 is displayed next to the lower side of each medical image, an examination added to a3, b3, and c3 is displayed next to the right side of each medical image, and an examination added to a4, b4, and c4 is displayed next to the upper side of each medical image.

In addition, when a thumbnail image 103*a* is dragged and dropped into a5, b5, or c5, the divided region setting section 32*c* displays a medical image 103 for the thumbnail image 103*a* in place of the medical images 100, 101 or 102, instead of additional display.

In addition, the divided region setting section 32*c* sets an overlap region d1 including the medical images 100, 101, and 102, and sets the display position of an additional examination in the overlap region d1 between the medical image 100 and the medical images 101 and 102 (interruption display). Therefore, when the thumbnail image 103*a* is dragged and dropped into the overlap region d1, the share window display control section 32*b* divides the full screen of the share window 90*c* into three parts in a horizontal direction, and displays the medical image 100 on the right screen, the thumbnail image 103 corresponding to the thumbnail image 103*a* on the middle screen, and the medical images 101 and 102 on the left screen. The left screen is further divided in a vertical direction and is displayed in the same manner as the share window 90*c*. That is, the medical image 102 is displayed on the upper screen, and the medical image 101 is displayed on the lower screen. As a result, the share window 90*c* changes to the share window 90*d*.

Figure 19:
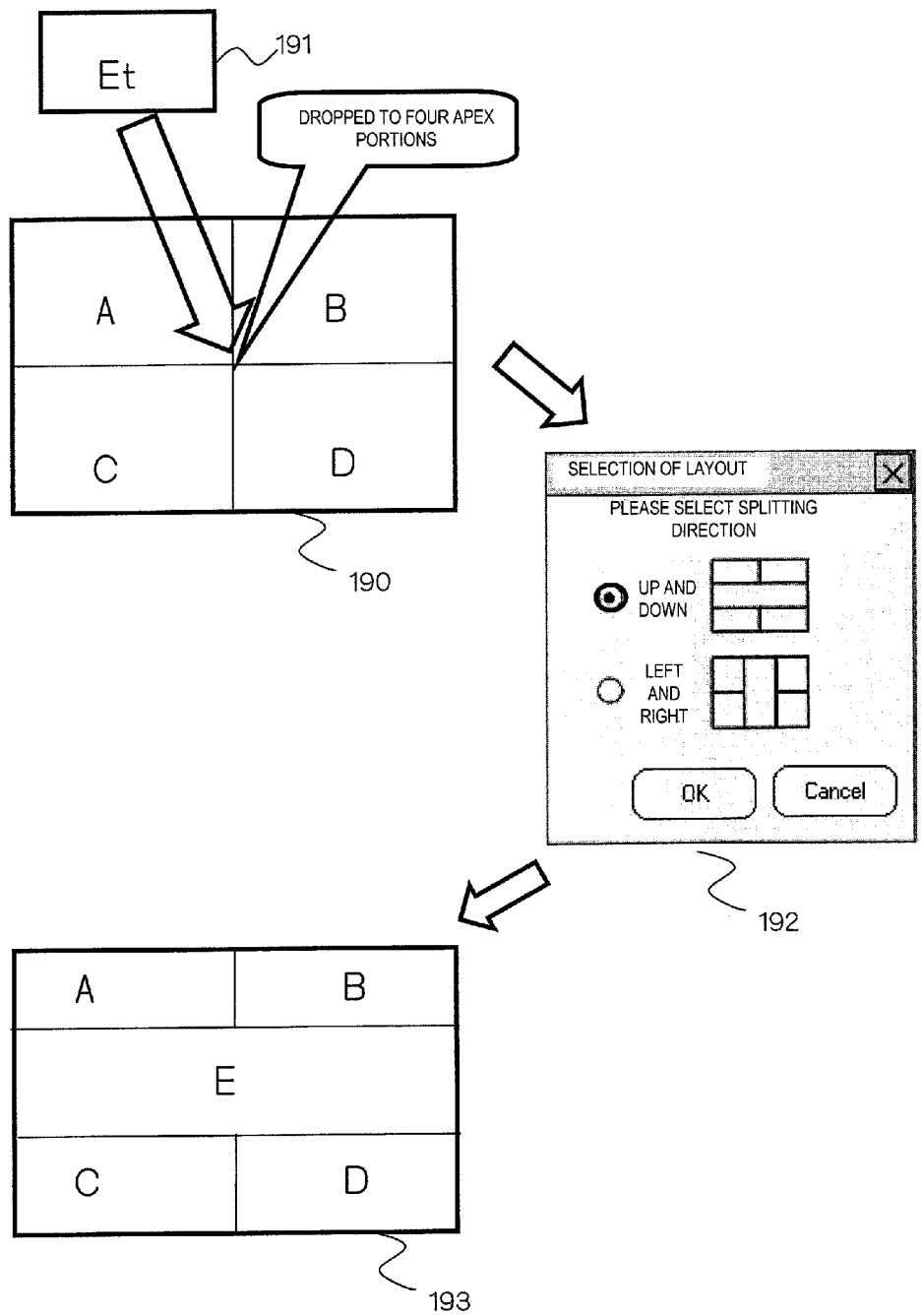
FIG. 19 is an explanatory view showing a division method in a state where the apices of four divided parts are in contact with each other.

Next, layout change of the divided region setting section 32*c* will be described on the basis of FIGS. 17 to 19. FIG. 17 is an explanatory view showing the percentages and regions of layout division positions, FIG. 18 is an explanatory view of layer change based on FIG. 17, and FIG. 19 is an explanatory view showing a division method in a state where the apices of four divided parts are in contact with each other.

A rectangular region 170 (hereinafter, referred to as a "display area 170") which is an image display area in FIG. 17 is equivalent to each display area of the medical images 100 and 101 in FIG. 16 and each display area of medical images 91*h*, 91*i*, 91*j*, and 91*k* in FIG. 20 which will be described later. In addition, dotted lines in the display area 170 are the same as dotted lines in the display areas of the medical images 100 and 101 in FIG. 16. This display area 170 is divided into five regions of (e) to (i), regions (a) to (d) on the borderline of the display area 170, and four apices (j) to (m). The area on the borderline of (a) to (d) is formed as a region up to 10 pixels from the borderline. In addition, each of the regions (e) to (h) is formed by an inside region of the display area 170 which is located up to the length of 25% of the length of the side perpendicular to the borderline, which is included in each region, from the borderline. For example, the region (e) is a region including the left side and is formed by an inside region up to the length of 25% of the long side perpendicular to the left side (short side). The same is true for the regions (f), (g), and (h). As a result, the middle region (i) has borderlines located at the inner side from each borderline by 25% of the lengths of long and short sides, and is formed by a rectangular region in which the length of one side is 50% of the length of each of the long and short sides. Division of the display area is performed in units of a displayed image. Therefore, when no image is displayed in the display area 170, the entire display area 170 is divided into (a) to (m). When a plurality of images are displayed in the display area 170, each area where each image is displayed is divided into (a) to (m). The above numerical examples, such as 10 pixels, 25%, and 50%, are just examples, and the present invention is not limited to these numerical values.

In addition, as shown in Table 171, a pattern rule of image addition or replacement when a thumbnail image is dropped to the position are attached to each of (a) to (m). Data indicating this rule is stored in the main memory 11 or the magnetic disk 12, and the divided region setting section 32c performs layout change processing by referring to the data appropriately. In addition, Table 171 is just an example of the data structure indicating the rule, and the present invention is not limited to this.

In addition, although the display area 170 is divided into (a) to (m) when two images are displayed in the display area 170, the number of divisions of each area may be smaller than the number of (a) to (m) when the area where each image is displayed is reduced by displaying a larger number of images.

In addition, when the size of each area (size of a displayed image) is smaller than a predetermined size, not additional display but image replacement may be performed when a thumbnail image is dropped to a certain position of the area, instead of division. The number of divisions and the predetermined size at the time of layout change from additional display to image replacement may be appropriately set according to the size of a monitor or the size of the display area.

FIG. 18 shows layout change processing based on Table 171 in FIG. 17. In a so-called initial state where no image is displayed in the display area, an image A is displayed in the entire image display area even if a thumbnail image At of the thumbnail image A is dropped to one of the positions of (a) to (m) (refer to FIGS. 18(1) and 18(2)). When a thumbnail image Bt of an image B is dropped to, for example, c (on the borderline) in this state, the width of the display area of the image A is reduced, and the image A is moved to the left and the image B is additionally displayed on the right side of the image A (refer to FIG. 18(2)). In this case, the display area widths of the images A and B are adjusted automatically.

Here, when a thumbnail image Ct corresponding to an image C is dropped to c (on the borderline) (refer to FIG. 18(3-1)), the image C is added above the images A and B (refer to FIG. 18(4-1)). On the other hand, when the thumbnail image Ct is dropped to (f) (refer to FIG. 18(3-2)), the display area of the image B is divided, and the image C is additionally displayed in an upper portion of the divided region and the image B is displayed in a lower portion of the divided region. In this case, there is no change in the display mode of the image A.

Subsequently, when a thumbnail image Dt corresponding to an image D is dropped to (i) of the image C (refer to FIG. 18(5)), the images C and D are exchanged (refer to FIG. 18(6)). In FIG. 18, only the layout change processing according to the rule based on Table 171 when images are dropped to (c), (f), and (i) of the display area 170 has been described. However, the layout change processing is also the same for other regions described in Table 171. In addition, the rule of the layout change in FIGS. 17 and 18 is just an example, and the rule is not limited to FIGS. 17 and 18.

Next, a process prompting the user to select the layout when the divided region setting section 32c cannot determine uniquely the layout after change with the rule of Table 171 in FIG. 17 will be described on the basis of FIG. 19. As an example in which the divided region setting section 32c cannot determine uniquely the layout after change, there may be a case where four images A, B, C, and D are displayed in the same size and a thumbnail image Et 191 is dropped to an apex portion of the four images, for example, like a display area 190 in FIG. 19. In this case, there are a mode in which the display area 190 is divided up and down and a mode in which the display area 190 is divided into left and right portions. For this reason, the divided region setting section 32c cannot determine the layout uniquely. Therefore, the divided region setting section 32c displays a layout selection screen 192 and displays candidates of the layout change so that the user select it. Then, the layout change is performed according to the selected layout. In FIG. 19, on the layout selection screen 192, a layout which divides the display area 190 into three stages along the vertical direction is selected. Accordingly, the divided region setting section 32c divides the display area 190 vertically into three stages and displays the images A and B side by side horizontally in the upper stage, displays only the image E in the middle stage, and displays the images C and D side by side horizontally in the lower stage.

As described above, the user can display examinations corresponding to thumbnail images or examination icons of the history area 70 additionally in the share window 90 by dragging and dropping these thumbnail images or examination icons using the mouse 19. In addition, when performing the additional display, the display position of the examination displayed additionally can be designated by the dropping position. Therefore, additional display can be performed at the position according to the user's preference. In addition, although the additional display is designated by drag-and-drop operation in the present embodiment, the operation is not limited to this.

Then, a process of deleting a displayed examination from the share window 90 will be described using FIG. 16. A case where the medical image 103 (to which a dotted square frame is added) displayed in the middle of the screen is deleted from the share window 90d will be described as an example. A user moves a mouse cursor (not shown) to the medical image 103 and right-clicks to select "delete" from the pull-down menu. The share window display control section 32b deletes a selected examination and also performs screen size readjustment for increasing the screen size of an examination displayed adjacent to the medical image 103 to be deleted (in the share window 90d, medical images 100, 101, and 102) according to the screen size of the medical image 103 to be deleted.

As a result, the share window 90d changes to the share window 90c1.

When the user performs an operation to delete the medical image 102 further in this state, the share window display control section 32b deletes the medical image 102 and also readjusts the screen size of the examination displayed adjacent to the medical image 102. In the share window 90c1, as examinations adjacent to the medical image 102 to be deleted, there are the medical images 100 and 101. In FIG. 16, however, only the screen size of the medical image 101 adjacent to the long side of the medical image 102 is changed. As a result, the share window 90c1 changes to the share window 90b1.

As described above, it is possible to delete an examination, which does not need to be displayed, of examinations displayed in the share window 90 when necessary while increasing the screen size of a remaining displayed examination.

Display Change 8: Layout Change of the Share Window

A layout showing the display position of an examination in one or more share windows is stored in the layout storage section 33 for each routine, and the display position of the share window 90 may be changed along the layout selected by the user.

Here, the "routine" is defined as follows. Here, the "routine" is used in the meaning of a function allowing the routine diagnostic procedures, which are performed in daily routine by a doctor, to be reproduced by simple operations. For example, in the case of a diagnosis of a CT examination, when this image is displayed first and then a previous image is displayed and this image and the previous image are finally displayed side by side in the vertical direction, a function allowing these image display positions to be changed by one operation is the "routine".

Hereinafter, a layout change of the share window will be described on the basis of FIG. 20. FIG. 20 is a schematic diagram showing the layout selection screen of the share window, and shows an example of screen display in a state where the "layout selection" button 92 of the share window 90 in FIG. 9 is pressed.

Figure 20:
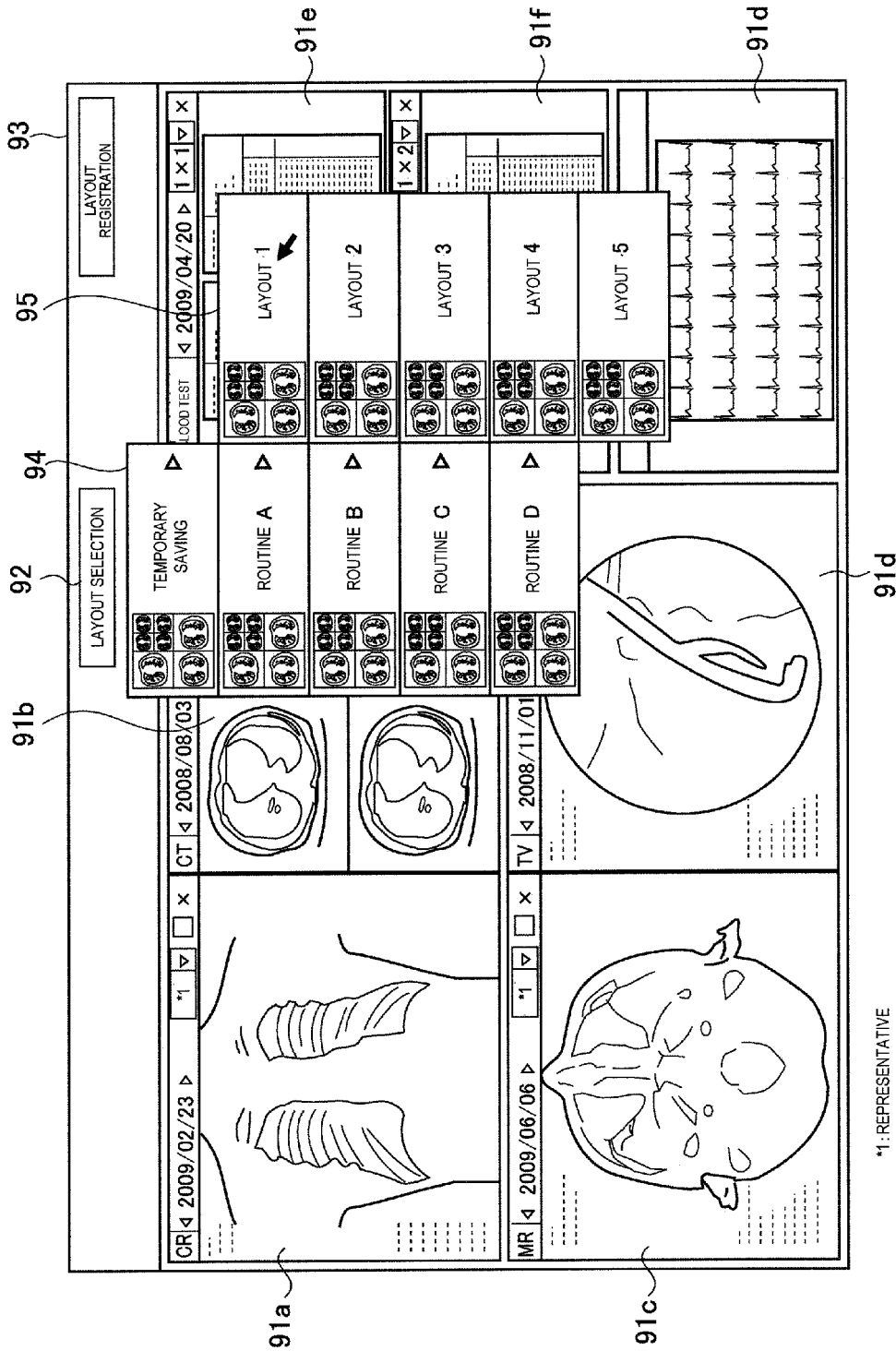
FIG. 20 is a schematic diagram showing a layout selection screen of a share window.

When the user clicks the "layout selection" button 92 in FIG. 9, the state changes to FIG. 20. In FIG. 20, a pull-down menu 94 of routine names and a pull-down menu 95 of layouts corresponding to the respective routines are displayed beside the "layout selection" button 92. Although the pull-down menu 94 of routine names and the pull-down menu 95 of layouts are present on an examination data operation screen 90 in the present embodiment, the pull-down menu 94 of routine names and the pull-down menu 95 of layouts may also be present on the image display screen of an image viewer instead of the examination data operation screen 90. On the initial screen of the share window of the present embodiment, a layout in which medical images 91a to 91d and examination data 91e to 91d are displayed is selected for the routine name "colon cancer". However, when the user selects "layout 1" corresponding to "routine A", the layout selection section 32e reads the "layout 1" corresponding to the "routine A" from the reference candidate/protocol/layout storage section 33, and the reference candidate extraction section 32a extracts examinations included in the layout 1, among the examination information of the object stored in the main memory 11 or the magnetic disk 12, as reference candidates. Then, the share window display control section 32b arrays the reference candidates extracted along the layout 1 in the share window 90. In the case of the layout 1, a change to the layout in which CT images are displayed as shown in the pull-down menu 95 is made.

In addition, when the user clicks a button of "layout registration" 93 after adding/deleting an examination for the reference candidate of the share window 90 as in the display change 7 described above, the layout generation section 32d generates the layout after addition/deletion of the examination by the user as a new layout and stores the generated layout in the reference candidate/protocol/layout storage section 33 so as to match the routine name (although this is "colon cancer" in the initial state of the present embodiment, the routine name may appropriately be input from the input screen (not shown)). In this manner, the addition of a layout becomes possible. In addition, when "temporary saving" on the top of the pull-down menu 94 is clicked, the share window 90 displayed at the time of clicking is saved as a temporary layout. By selecting the "temporary saving" again after performing addition/deletion of an examination in this state, the state can return to a display state of the share window saved temporarily recently. In addition, although it has been described that the state can return to a display state of the share window saved temporarily recently when the "temporary saving" is selected, it is possible to change the content of the share window according to the control on the image display screen side, that is, switching of the image display screen.

(Step S621)

Figure 21:
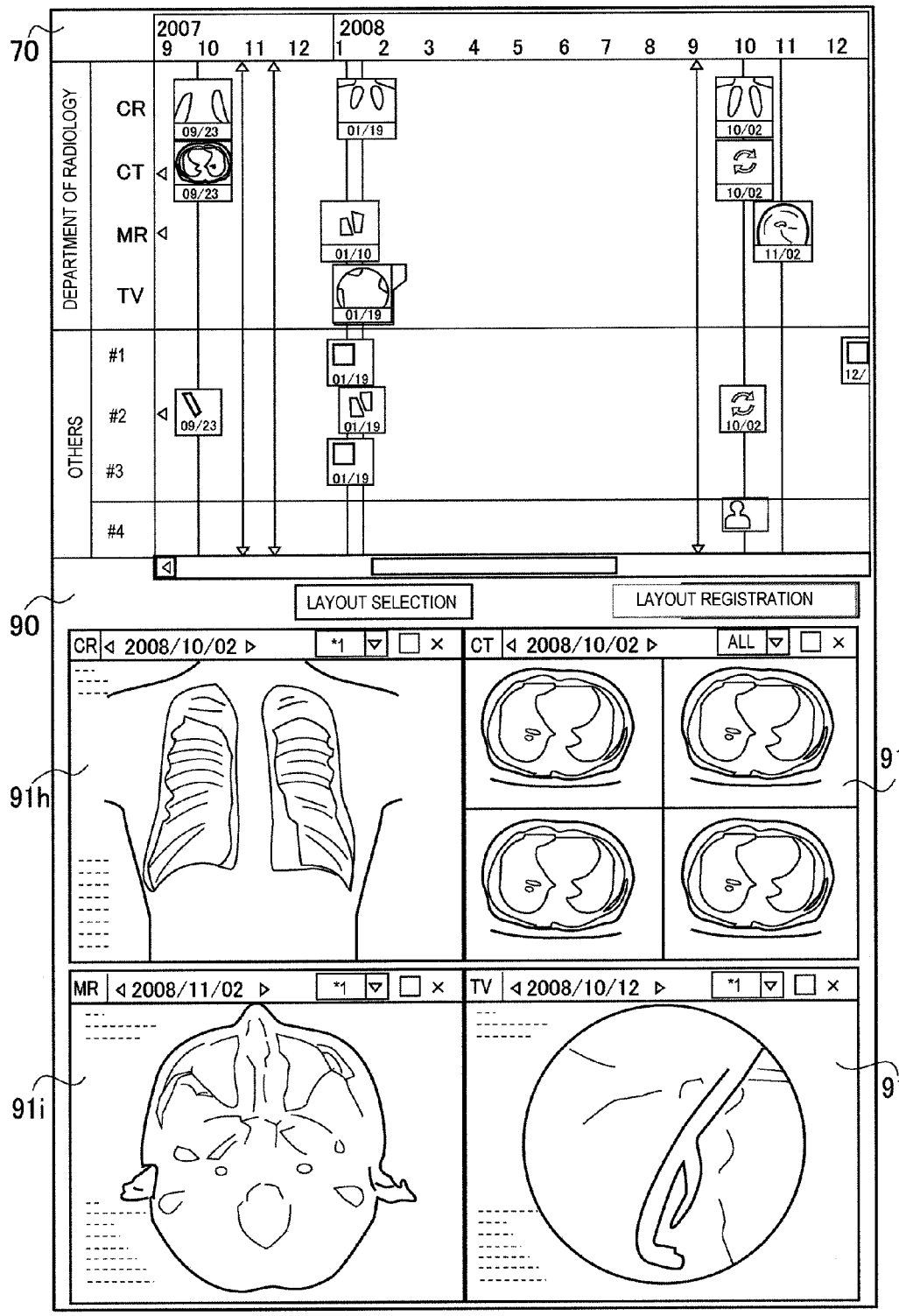
FIG. 21 is an explanatory view showing the processing of displaying the newest examination at an arbitrary point in time in the history area.
Figure 22:
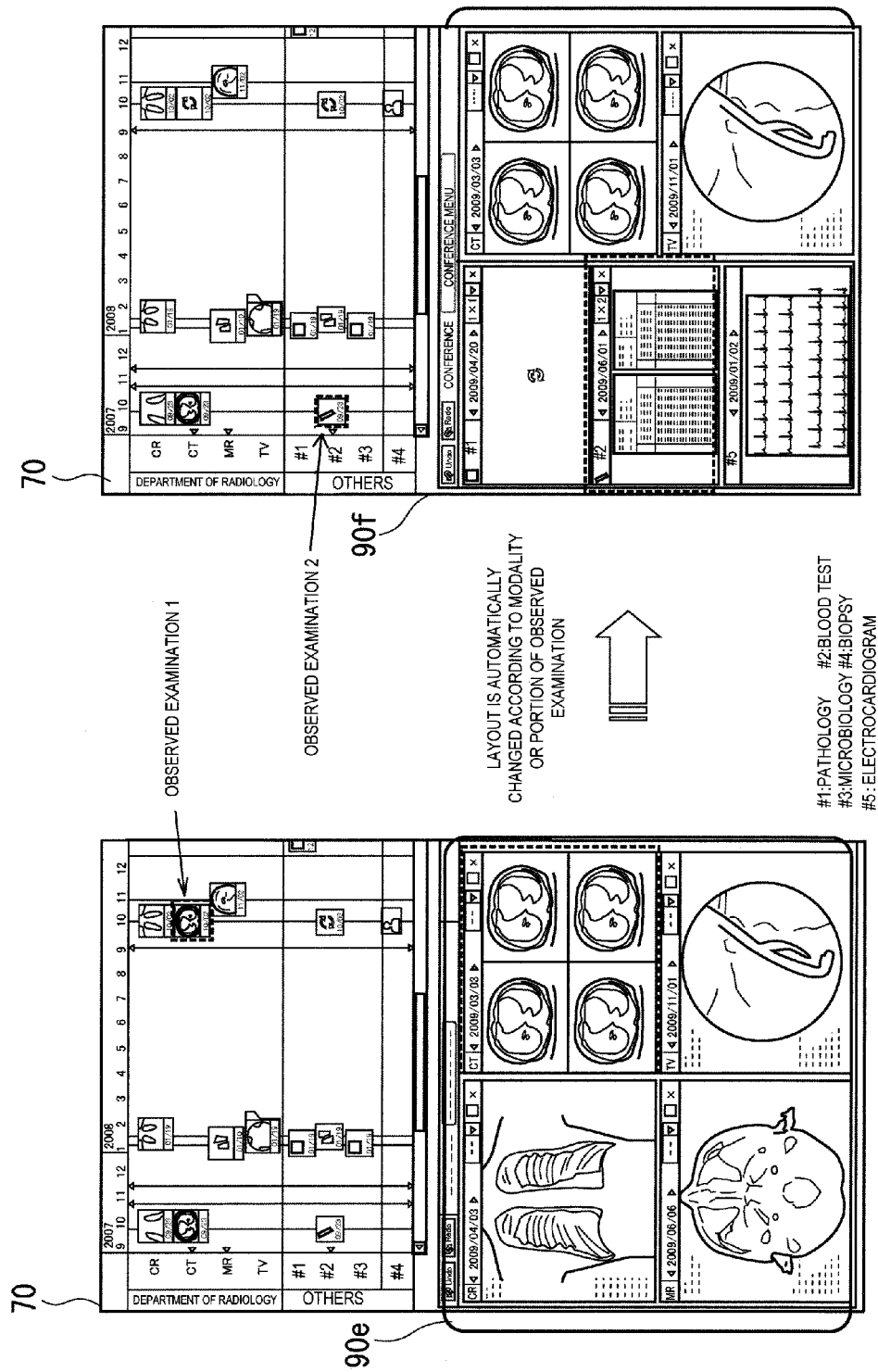
FIG. 22 is an explanatory view showing the processing of selecting a new reference image in the history area.

Hereinafter, an example in which the history area and the share window are linked to each other to change the display will be described on the basis of FIGS. 21 and 22. FIG. 21 is an explanatory view showing the processing of displaying a newest examination at an arbitrary point in time in the history area, and FIG. 22 is an explanatory view showing the processing of selecting a new reference image in the history area.

In the history area 70, the history of other examinations is displayed with the reference image as a newest image in the initial state. However, it is also possible to display a reading screen with a certain past examination as a reference image. In the present embodiment, with a CT image of Jun. 6, 2009 as a reference image, a chest CR image 91a of Feb. 23, 2009, an abdomen CT image 91b of Mar. 3, 2008, a head MRI image 91c of Jun. 6, 2009, a heart IVR image 91d of Nov. 1, 2008, blood test data 91e of Apr. 20, 2009, blood test data 91f of Jun. 1, 2009, and electrocardiogram of Feb. 2, 2009 shown in FIG. 9 are extracted as reference candidates and are displayed in the share window 90.

In this state, in the example shown in FIG. 21, the user right-clicks at an arbitrary position on the display area of the history area 70 and selects "display the newest examination at this point in time". Here, a point in time of Dec. 1, 2008 is selected.

The reference candidate extraction section 32a extracts a newest examination at the selected point in time from the main memory 11 or the magnetic disk 12. In the present embodiment, a chest CR image 91h of Oct. 2, 2008, a head MRI image 91i of Nov. 2, 2008, a chest CT image 91j of Oct. 2, 2008, and a heart IVR image 91k of Oct. 2, 2008 are extracted.

From the extracted examination information 91h, the share window display control section 32b replaces 91k with the image displayed in the share window 90 and displays it.

By executing "display the newest examination at this point in time", the user can easily refer to the newest examination image at a certain point in time in the past. Accordingly, since a situation at that time can be reproduced on the examination data operation screen 60, it can be helpful to the diagnosis.

In addition, as shown in FIG. 22, when the user selects a thumbnail image or an examination icon for an observed examination 2 in a state where a share window 90e is displayed for an observed examination 1 in the history area 70, processing in steps S5111 to S513 is executed for the newly selected thumbnail image or examination icon and the share window 90e on the left side in FIG. 22 changes to a share window 90f on the right side. In this manner, it is possible to select a new reference image in the history area and to check the examination information of the reference candidate (by the modality or portion of an observed examination, the layout is changed automatically).

According to the present embodiment, the examination history of the object can be displayed along the time series of examination date and the information of examinations and the object. As a result, it becomes easy to see the examination history. In addition, since a reference image and examination information, which is a candidate compared with the reference examination, are displayed together, comparative reading or reference becomes easy.

The above embodiment has been described using the examination information display system 8 in which the modality 1, the image workstation 2, the image inspection terminal 3, the image server 4, the examination data server 5, and the reading terminal 6 are connected to each other through the network 7. However, also in an image display device of the reading terminal 6 which is not connected to the network, that is, the reading terminal 6 which has a so-called stand-alone configuration, the same display control processing as in the display control in the above-described embodiment may be performed by providing the reading terminal 6 with a storage unit that stores image data or examination information so that the desired examination information to be referred to is extracted from the storage unit.

Moreover, in the above-described embodiment, the display area where a reference image is displayed is configured as a window by denoting it as a "share window". However, the configuration of the display area is not limited to the window configuration, and the display area may also be formed by regions generated by forming insets of the screen, that is, examination data operation screens using one screen (one window) and dividing a part of the screen. The same is true for the history area.

REFERENCE SIGNS LIST

1: medical image capturing apparatus (modality)
2: image workstation
3: image inspection terminal
3a, 3b: image display device
4: image server
5: examination data server
6: reading terminal
6a, 6b: image display device
7: network
8: examination information display system

The invention claimed is:

1. An examination information display device comprising:
a processor;
a non-transitory storage medium,
wherein the processor causes the non-transitory storage medium to store examination information of an object with supplementary information of the examination information;
a display unit having a display screen on which the examination information is displayed;
a selection unit that selects a reference examination to be diagnosed from the examination information; and
an extraction unit that extracts candidate examination information, which is a candidate referred to or compared with the reference examination from the examination information by using supplementary information of the reference examination,
wherein the processor causes the non-transitory storage medium to store a layout that sets display position patterns of the candidate examination information, and
wherein the display unit has a share window that displays the candidate examination information according to the layout.

2. The examination information display device according to claim 1, further comprising:
a reference candidate non-transitory storage medium,
wherein the processor causes the reference candidate non-transitory storage medium to stores an examination type of a reference candidate corresponding to at least one of an examination type of the reference examination and an diagnostic object of the reference examination, and
wherein the extraction unit reads an examination type of a reference candidate corresponding to the reference examination from the reference candidate non-transitory storage medium and extracts candidate examination information of the object corresponding to the examination type from the non-transitory storage medium.

3. The examination information display device according to claim 1, further comprising:
a layout non-transitory storage medium,
wherein the processor causes the layout non-transitory storage medium to store a layout showing a display position of the examination information in the predetermined display region, the layout corresponding to at least one of an examination type of the reference examination and a reference order of the examination information in diagnosis of the reference examination, and
wherein a display control unit reads a layout corresponding to the reference examination from the layout storage unit and displays examination information of the reference candidate in the predetermined display region along the layout.

4. The examination information display device according to claim 1, further comprising:
a divided region setting unit that divides the predetermined display region into a plurality of divided regions and sets a display position of examination information, which is additionally displayed in the predetermined display region, for each divided region; and
an operating unit that inputs designation of an arbitrary position of the predetermined display region and an instruction to display new examination information additionally,
wherein a display control unit divides the predetermined display region into a plurality of screen regions in response to an instruction through the operating unit, changes a screen size of the new examination information and a screen size of examination information displayed in the predetermined display region according to sizes of the divided screen regions, additionally displays the new examination information in a screen region including the designated position, and displays the examination information displayed in the predetermined display region again in other screen regions.

5. The examination information display device according to claim 4,
wherein the operating unit is means configured to drag and drop a thumbnail image or an icon of a medical image, which is displayed on the display unit, to the arbitrary position, and
wherein the display control unit displays examination information, which corresponds to the thumbnail image or the icon of the medical image dragged and dropped by the operating unit, additionally in a screen region including the drag-and-drop position.

6. The examination information display device according to claim 5,
wherein the operating unit performs an operation of selecting a thumbnail image or an icon of the medical image and setting the thumbnail image or the icon as a new reference examination, and
wherein the display control unit displays a reference candidate corresponding to the new reference examination in the predetermined display region.

7. The examination information display device according to claim 1,
wherein a display control unit displays a thumbnail image or an icon of a medical image showing examination information of the object in a different display region from the predetermined display region of the display screen,
wherein the operating unit selects and sets an arbitrary point in time in the past in the different display region, wherein the extraction unit extracts examination information as a reference candidate corresponding to examination information at the arbitrary point in time in the past, and wherein the display control unit displays the extracted examination information as a reference candidate corresponding to the examination information at the arbitrary point in time.

8. The examination information display device according to claim 7, wherein the extraction unit extracts examination information as a reference candidate corresponding to newest examination information at the arbitrary point in time in the past, and wherein the display control unit displays the extracted examination information as a reference candidate corresponding to the newest examination information at the arbitrary point in time.

9. The examination information display device according to claim 1, wherein the operating unit is means configured to select arbitrary examination information displayed in the predetermined display region and input an instruction to delete the selected examination information, and wherein a display control unit deletes the selected examination information from the predetermined display region in response to the instruction through the operating unit, changes a screen size of the examination information displayed in the predetermined display region to a size including a screen region of the deleted examination information, and displays the examination information with the changed size again.

10. The examination information display device according to claim 4, wherein the display control unit displays an examination history area whose horizontal axis is a time axis indicating an examination date of a medical image and examination data and vertical axis is an information axis indicating object attributes or examination attributes in the plurality of divided screen regions.

11. The examination information display device according to claim 10, wherein the display control unit displays a history area, in which thumbnail images of a medical image and an examination icon showing examination data are arrayed, in the examination history area.

12. The examination information display device according to claim 11, wherein the operating unit sets a time axis indicating time series of the examination date of the examination data, and also selects examination attributes or object attributes of examination information and a reference examination and sets an information axis based on the attributes.

13. The examination information display device according to claim 12, wherein the extraction unit extracts a thumbnail image of a medical image or an examination icon, which is arrayed in the examination history area, according to a disease name or a symptom of the object, and wherein the display control unit displays a reference order of examination information of the examination history area along a reference procedure corresponding to a user and a reference examination.

14. The examination information display device according to claim 13, wherein the operating unit performs an operation to drag and drop a thumbnail image of a medical image displayed in the history area into a region of a share window, and wherein the display control unit displays a medical image, which corresponds to the thumbnail image of the medical image, additionally on the basis of a display position of an added reference candidate set in the region of the share window.

15. An examination information display method comprising:

executing, by a processor, a step of storing examination information of an object with supplementary information of the examination information in a non-transitory storage medium;

selecting a reference examination to be diagnosed from the examination information;

extracting candidate examination information, which is a candidate referred to or compared with the reference examination from the examination information by using supplementary information of the examination information; and displaying the extracted candidate examination information according to the layout in a share window of a display screen of a display unit.

16. An examination information display device comprising:

a processor;

a non-transitory storage medium, where the processor causes the non-transitory storage medium to store examination information of an object;

a display unit that has a display screen on which the plurality of examination information is displayed;

an operating unit that drags and drops a thumbnail image or an icon of the examination information to the display unit; and a display control unit that changes a layout of the examination information displayed on the display unit according to the operation of the operating unit, wherein each display region for displaying examination information is divided into a plurality of areas, the non-transitory storage medium stores a rule of layout-changing that is set in each area, and the display control unit changes the layout according to the rule set in the area the thumbnail image or the icon dragged and dropped.

* * * * *